US008435551B2

(12) United States Patent
Semler et al.

(10) Patent No.: US 8,435,551 B2
(45) Date of Patent: May 7, 2013

(54) CANCELLOUS CONSTRUCT WITH SUPPORT RING FOR REPAIR OF OSTEOCHONDRAL DEFECTS

(75) Inventors: Eric J. Semler, Piscataway, NJ (US); Roman Shikhanovich, Edison, NJ (US); Alex B. Callahan, Perth Amboy, NJ (US); Katherine Gomes Truncale, Hillsborough, NJ (US); Judith I. Yannariello-Brown, Somerset, NJ (US); Yen-Chen Huang, East Brunswick, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 645 days.

(21) Appl. No.: 12/508,892

(22) Filed: Jul. 24, 2009

(65) Prior Publication Data

US 2010/0015202 A1    Jan. 21, 2010

Related U.S. Application Data

(63) Continuation-in-part of application No. 12/043,001, filed on Mar. 5, 2008, now abandoned, and a continuation-in-part of application No. 12/381,072, filed on Mar. 5, 2009.

(60) Provisional application No. 60/904,809, filed on Mar. 6, 2007, provisional application No. 61/189,252, filed on Aug. 15, 2008, provisional application No. 61/205,433, filed on Jan. 15, 2009.

(51) Int. Cl.
*A61F 2/28* (2006.01)

(52) U.S. Cl.
USPC .......................................... 424/423; 424/400

(58) Field of Classification Search ................. 424/400, 424/423
See application file for complete search history.

(56) References Cited

U.S. PATENT DOCUMENTS

| 3,400,199 | A | 9/1968 | Balassa |
| 3,476,855 | A | 11/1969 | Balassa |
| 3,478,146 | A | 11/1969 | Balassa |
| 3,551,560 | A | 12/1970 | Theile |
| 3,772,432 | A | 11/1973 | Balassa |
| 3,867,728 | A | 2/1975 | Stubstad et al. |
| 3,966,908 | A | 6/1976 | Balassa |
| 4,060,081 | A | 11/1977 | Yannas et al. |
| 4,172,128 | A | 10/1979 | Thiele et al. |
| 4,201,845 | A | 5/1980 | Feder et al. |
| 4,296,100 | A | 10/1981 | Franco |
| 4,378,347 | A | 3/1983 | Franco |
| 4,394,370 | A | 7/1983 | Jefferies |
| 4,400,833 | A | 8/1983 | Kurland |
| 4,442,655 | A | 4/1984 | Stroetmann |
| 4,458,678 | A | 7/1984 | Yannas et al. |
| 4,479,271 | A | 10/1984 | Bolesky et al. |
| 4,501,269 | A | 2/1985 | Bagby |
| 4,505,266 | A | 3/1985 | Yannas et al. |
| 4,600,574 | A | 7/1986 | Lindner et al. |
| 4,609,551 | A | 9/1986 | Caplan et al. |
| 4,627,853 | A | 12/1986 | Campbell et al. |
| 4,642,120 | A | 2/1987 | Nevo et al. |
| 4,656,137 | A | 4/1987 | Balassa |
| 4,681,763 | A | 7/1987 | Nathanson et al. |
| 4,683,195 | A | 7/1987 | Mullis et al. |
| 4,683,202 | A | 7/1987 | Mullis |
| 4,757,017 | A | 7/1988 | Cheung |
| 4,776,173 | A | 10/1988 | Kamarei et al. |
| 4,776,853 | A | 10/1988 | Klement et al. |
| 4,795,467 | A | 1/1989 | Piez et al. |
| 4,801,299 | A | 1/1989 | Brendel et al. |
| 4,837,379 | A | 6/1989 | Wienberg |
| 4,846,835 | A | 7/1989 | Grande |
| 4,880,429 | A | 11/1989 | Stone |
| 4,902,508 | A | 2/1990 | Badylak et al. |
| 4,904,259 | A | 2/1990 | Itay |
| 4,932,973 | A | 6/1990 | Gendler |
| 4,950,296 | A | 8/1990 | McIntyre |
| 4,950,483 | A | 8/1990 | Ksander et al. |

(Continued)

FOREIGN PATENT DOCUMENTS

| EP | 0517030 A2 | 12/1992 |
| EP | 0522569 A1 | 1/1993 |

(Continued)

OTHER PUBLICATIONS

Sedgwick et al., "Studies into the influence of carrageenan-induced inflammation on articular cartilage degradation using implantation into air pouches", British Journal of Experimental Pathology, vol. 66, (1985), pp. 445-453.
First Action Interview Pilot Program Pre-interview Communications for U.S. Appl. No. 12/696,366, mailed Oct. 13, 2011.
Non-final Office Action for U.S. Appl. No. 12/881,988, mailed Oct. 26, 2011.
Non-final Office Action for U.S. Appl. No. 11/081,103, mailed Nov. 28, 2011.
Non-Final Office Action for U.S. Appl. No. 11/081,103, mailed Jan. 14, 2010.
Final Office Action for U.S. Appl. No. 11/481,955, mailed Jan. 7, 2010.
Final Office Action for U.S. Appl. No. 11/657,042, mailed Dec. 28, 2009.

(Continued)

*Primary Examiner* — Ruth Davis
(74) *Attorney, Agent, or Firm* — Greenberg Traurig, LLP

(57) ABSTRACT

The invention is directed toward an osteochondral repair assembly comprising a shaped allograft construct comprising an unbalanced barbell-shaped cylindrical cancellous bone primary member formed with a mineralized cylindrical base section having a smaller diameter cylindrical stem leading to a second cylindrical section which is demineralized. A mineralized ring-shaped support member is forced over the compressed demineralized second demineralized the aperture of the ring-shaped member to fit around the stem with one ring surface being adjacent the bottom surface to the second cylindrical section and the opposite ring surface being adjacent the upper surface of the mineralized cylindrical base section.

21 Claims, 5 Drawing Sheets

U.S. PATENT DOCUMENTS

| | | | |
|---|---|---|---|
| 4,955,911 A | 9/1990 | Frey et al. |
| 4,963,146 A | 10/1990 | Li |
| 4,963,489 A | 10/1990 | Naughton et al. |
| 4,965,188 A | 10/1990 | Mullis et al. |
| 4,971,954 A | 11/1990 | Brodsky et al. |
| 4,976,738 A | 12/1990 | Frey et al. |
| 4,978,355 A | 12/1990 | Frey et al. |
| 4,994,559 A | 2/1991 | Moscatelli et al. |
| 5,002,071 A | 3/1991 | Harrell |
| 5,002,583 A | 3/1991 | Pitaru et al. |
| 5,007,934 A | 4/1991 | Stone |
| 5,032,508 A | 7/1991 | Naughton et al. |
| 5,041,138 A | 8/1991 | Vacanti et al. |
| 5,053,049 A | 10/1991 | Campbell |
| 5,053,050 A | 10/1991 | Itay |
| 5,067,963 A | 11/1991 | Khouri et al. |
| 5,067,964 A | 11/1991 | Richmond et al. |
| 5,073,373 A | 12/1991 | O'Leary et al. |
| 5,084,051 A | 1/1992 | Tormala et al. |
| 5,092,887 A | 3/1992 | Gendler |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A | 3/1993 | Gersberg |
| 5,206,023 A | 4/1993 | Hunziker |
| 5,226,914 A | 7/1993 | Caplan et al. |
| 5,236,456 A | 8/1993 | O'Leary et al. |
| 5,256,140 A | 10/1993 | Fallick |
| 5,260,420 A | 11/1993 | Burnouf-Radosevich et al. |
| 5,266,476 A | 11/1993 | Sussman et al. |
| 5,270,300 A | 12/1993 | Hunziker |
| 5,275,826 A | 1/1994 | Badylak et al. |
| 5,281,422 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,354,557 A | 10/1994 | Oppermann et al. |
| 5,356,629 A | 10/1994 | Sander et al. |
| 5,368,858 A | 11/1994 | Hunziker |
| 5,372,821 A | 12/1994 | Badylak et al. |
| 5,380,328 A | 1/1995 | Morgan |
| 5,411,885 A | 5/1995 | Marx |
| 5,425,769 A | 6/1995 | Snyders, Jr. |
| 5,439,684 A | 8/1995 | Prewett et al. |
| 5,439,818 A | 8/1995 | Fiddes et al. |
| 5,443,950 A | 8/1995 | Naughton et al. |
| 5,445,833 A | 8/1995 | Badylak et al. |
| 5,464,439 A | 11/1995 | Gendler |
| 5,466,462 A | 11/1995 | Rosenthal et al. |
| 5,491,220 A | 2/1996 | Seddon et al. |
| 5,496,722 A | 3/1996 | Goodwin et al. |
| 5,507,813 A | 4/1996 | Dowd et al. |
| 5,510,396 A | 4/1996 | Prewett et al. |
| 5,512,460 A | 4/1996 | Nauro et al. |
| 5,513,662 A | 5/1996 | Morse et al. |
| 5,516,532 A | 5/1996 | Atala et al. |
| 5,516,533 A | 5/1996 | Badylak et al. |
| 5,545,222 A | 8/1996 | Bonutti |
| 5,549,904 A | 8/1996 | Juergensen et al. |
| 5,554,389 A | 9/1996 | Badylak et al. |
| 5,556,430 A | 9/1996 | Gendler |
| 5,569,272 A | 10/1996 | Reed et al. |
| 5,571,895 A | 11/1996 | Kurokawa et al. |
| 5,576,288 A | 11/1996 | Lappi et al. |
| 5,604,293 A | 2/1997 | Fiddes et al. |
| 5,607,474 A | 3/1997 | Athanasiou et al. |
| 5,614,496 A | 3/1997 | Dunstan et al. |
| 5,618,925 A | 4/1997 | Dupont et al. |
| 5,622,928 A | 4/1997 | Naruo et al. |
| 5,624,463 A | 4/1997 | Stone et al. |
| 5,631,011 A | 5/1997 | Wadstrom |
| 5,632,745 A | 5/1997 | Schwartz |
| 5,656,598 A | 8/1997 | Dunstan et al. |
| 5,662,710 A | 9/1997 | Bonutti |
| 5,679,637 A | 10/1997 | Lappi et al. |
| 5,681,353 A | 10/1997 | Li et al. |
| 5,695,998 A | 12/1997 | Badylak et al. |
| 5,700,476 A | 12/1997 | Rosenthal et al. |
| 5,700,774 A | 12/1997 | Hattersley et al. |
| 5,707,962 A | 1/1998 | Chen et al. |
| 5,713,374 A | 2/1998 | Pachence et al. |
| 5,716,413 A | 2/1998 | Walter et al. |
| 5,723,331 A | 3/1998 | Tubo et al. |
| 5,733,337 A | 3/1998 | Carr, Jr. et al. |
| 5,736,132 A | 4/1998 | Juergensen et al. |
| 5,736,372 A | 4/1998 | Vacanti et al. |
| 5,736,396 A | 4/1998 | Bruder et al. |
| 5,749,874 A | 5/1998 | Schwartz |
| 5,755,791 A | 5/1998 | Whitson et al. |
| 5,759,190 A | 6/1998 | Vibe-Hansen et al. |
| 5,769,899 A | 6/1998 | Schwartz et al. |
| 5,770,417 A | 6/1998 | Vacanti et al. |
| 5,782,835 A | 7/1998 | Hart et al. |
| 5,782,915 A | 7/1998 | Stone |
| 5,786,217 A | 7/1998 | Tubo et al. |
| 5,788,625 A | 8/1998 | Plouhar et al. |
| 5,800,537 A | 9/1998 | Bell |
| 5,814,084 A | 9/1998 | Grivas et al. |
| 5,842,477 A | 12/1998 | Naughton et al. |
| 5,846,931 A | 12/1998 | Hattersley et al. |
| 5,853,746 A | 12/1998 | Hunziker |
| 5,855,620 A | 1/1999 | Bishopric et al. |
| 5,859,208 A | 1/1999 | Fiddes et al. |
| 5,863,296 A | 1/1999 | Orton |
| 5,863,297 A | 1/1999 | Walter et al. |
| 5,866,415 A | 2/1999 | Villeneuve |
| 5,876,452 A | 3/1999 | Athanasiou et al. |
| 5,881,733 A | 3/1999 | Stone |
| 5,888,219 A | 3/1999 | Bonutti |
| 5,891,558 A | 4/1999 | Bell et al. |
| 5,893,888 A | 4/1999 | Bell |
| 5,899,936 A | 5/1999 | Goldstein |
| 5,899,939 A | 5/1999 | Boyce et al. |
| 5,904,716 A | 5/1999 | Gendler |
| 5,906,827 A | 5/1999 | Khouri et al. |
| 5,910,315 A | 6/1999 | Stevenson et al. |
| 5,916,265 A | 6/1999 | Hu |
| 5,922,028 A | 7/1999 | Plouhar et al. |
| 5,948,429 A | 9/1999 | Bell et al. |
| 5,955,438 A | 9/1999 | Pitaru et al. |
| 5,964,805 A | 10/1999 | Stone |
| 5,972,368 A | 10/1999 | McKay |
| 5,972,385 A | 10/1999 | Liu et al. |
| 5,974,663 A | 11/1999 | Ikeda et al. |
| 5,989,269 A | 11/1999 | Vibe-Hansen et al. |
| 5,989,289 A | 11/1999 | Coates et al. |
| 5,989,866 A | 11/1999 | Deisher et al. |
| 5,998,170 A | 12/1999 | Arakawa et al. |
| 6,001,352 A | 12/1999 | Boyan et al. |
| 6,005,161 A | 12/1999 | Brekke et al. |
| 6,013,853 A | 1/2000 | Athanasiou et al. |
| 6,017,348 A | 1/2000 | Hart et al. |
| 6,025,334 A | 2/2000 | Dupont et al. |
| 6,025,538 A | 2/2000 | Yaccarino, III |
| 6,027,743 A | 2/2000 | Khouri et al. |
| 6,030,635 A | 2/2000 | Gertzman et al. |
| 6,037,171 A | 3/2000 | Larsson |
| 6,039,762 A | 3/2000 | McKay |
| 6,056,777 A | 5/2000 | McDowell |
| 6,060,640 A | 5/2000 | Pauley et al. |
| 6,074,663 A | 6/2000 | Delmotte et al. |
| 6,080,194 A | 6/2000 | Pachence et al. |
| 6,090,996 A | 7/2000 | Li |
| 6,090,998 A | 7/2000 | Grooms et al. |
| 6,096,081 A | 8/2000 | Grivas et al. |
| 6,096,347 A | 8/2000 | Geddes et al. |

| | | |
|---|---|---|
| 6,110,209 A | 8/2000 | Stone |
| 6,110,482 A | 8/2000 | Khouri et al. |
| 6,123,731 A | 9/2000 | Boyce et al. |
| 6,132,472 A | 10/2000 | Bonutti |
| 6,143,293 A | 11/2000 | Weiss et al. |
| 6,146,385 A | 11/2000 | Torrie et al. |
| 6,156,068 A | 12/2000 | Walter et al. |
| 6,165,486 A | 12/2000 | Marra et al. |
| 6,176,880 B1 | 1/2001 | Plouhar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,197,061 B1 | 3/2001 | Masuda et al. |
| 6,197,586 B1 | 3/2001 | Bhatnagar et al. |
| 6,200,347 B1 | 3/2001 | Anderson et al. |
| 6,221,854 B1 | 4/2001 | Radomsky |
| 6,231,607 B1 | 5/2001 | Ben-Bassat et al. |
| 6,235,316 B1 | 5/2001 | Adkisson |
| 6,242,247 B1 | 6/2001 | Rieser et al. |
| 6,251,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |
| 6,270,528 B1 | 8/2001 | McKay |
| 6,274,090 B1 | 8/2001 | Coelho et al. |
| 6,274,663 B1 | 8/2001 | Hosokawa et al. |
| 6,274,712 B1 | 8/2001 | Springer et al. |
| 6,280,473 B1 | 8/2001 | Lemperle et al. |
| 6,281,195 B1 | 8/2001 | Rueger et al. |
| 6,283,980 B1 | 9/2001 | Vibe-Hansen et al. |
| 6,288,043 B1 | 9/2001 | Spiro et al. |
| 6,293,970 B1 | 9/2001 | Wolfinbarger, Jr. |
| 6,294,187 B1 | 9/2001 | Boyce et al. |
| 6,294,359 B1 | 9/2001 | Fiddes et al. |
| 6,303,585 B1 | 10/2001 | Spiro et al. |
| 6,305,379 B1 | 10/2001 | Wolfinbarger, Jr. |
| 6,306,174 B1 | 10/2001 | Gie et al. |
| 6,306,177 B1 | 10/2001 | Felt et al. |
| 6,306,424 B1 | 10/2001 | Vyakarnam et al. |
| 6,310,267 B1 | 10/2001 | Rapp |
| 6,319,712 B1 | 11/2001 | Meenen et al. |
| 6,333,029 B1 | 12/2001 | Vyakanam et al. |
| 6,352,558 B1 | 3/2002 | Spector |
| 6,352,971 B1 | 3/2002 | Deisher et al. |
| 6,361,565 B1 | 3/2002 | Bonutti |
| 6,371,958 B1 | 4/2002 | Overaker |
| 6,376,244 B1 | 4/2002 | Atala |
| 6,379,367 B1 | 4/2002 | Vibe-Hansen et al. |
| 6,379,385 B1 | 4/2002 | Kalas et al. |
| 6,383,211 B1 | 5/2002 | Staehle |
| 6,387,693 B2 | 5/2002 | Rieser et al. |
| 6,398,811 B1 | 6/2002 | McKay |
| 6,398,816 B1 | 6/2002 | Breitbart et al. |
| 6,398,972 B1 | 6/2002 | Blasetti et al. |
| 6,432,436 B1 | 8/2002 | Gertzman et al. |
| 6,437,018 B1 | 8/2002 | Gertzman et al. |
| 6,440,141 B1 | 8/2002 | Philippon |
| 6,440,427 B1 | 8/2002 | Wadstrom |
| 6,440,444 B2 | 8/2002 | Boyce et al. |
| 6,451,060 B2 | 9/2002 | Masuda et al. |
| 6,454,811 B1 | 9/2002 | Sherwood et al. |
| 6,458,144 B1 | 10/2002 | Morris et al. |
| 6,458,158 B1 | 10/2002 | Anderson et al. |
| 6,458,375 B1 | 10/2002 | Gertzman et al. |
| 6,468,314 B2 | 10/2002 | Schwartz et al. |
| 6,471,993 B1 | 10/2002 | Shastri et al. |
| 6,475,175 B1 | 11/2002 | Rivera et al. |
| 6,486,377 B2 | 11/2002 | Rapp |
| 6,488,033 B1 | 12/2002 | Cerundolo |
| 6,489,165 B2 | 12/2002 | Bhatnagar et al. |
| 6,497,726 B1 | 12/2002 | Carter et al. |
| 6,503,277 B2 | 1/2003 | Bonutti |
| 6,504,079 B2 | 1/2003 | Tucker et al. |
| 6,511,511 B1 | 1/2003 | Slivka et al. |
| 6,511,958 B1 | 1/2003 | Atkinson et al. |
| 6,514,514 B1 | 2/2003 | Atkinson et al. |
| 6,520,964 B2 | 2/2003 | Tallarida et al. |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,548,729 B1 | 4/2003 | Seelich et al. |
| 6,569,172 B2 | 5/2003 | Asculai et al. |
| 6,576,015 B2 | 6/2003 | Geistlich et al. |
| 6,576,265 B1 | 6/2003 | Spievack |
| 6,579,538 B1 | 6/2003 | Spievack |
| 6,582,960 B1 | 6/2003 | Martin et al. |
| 6,591,581 B2 | 7/2003 | Schmieding |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,599,515 B1 | 7/2003 | Delmotte |
| 6,623,963 B1 | 9/2003 | Muller et al. |
| 6,626,950 B2 | 9/2003 | Brown et al. |
| 6,630,000 B1 | 10/2003 | Bonutti |
| 6,632,247 B2 | 10/2003 | Boyer, II et al. |
| 6,652,592 B1 | 11/2003 | Grooms et al. |
| 6,652,593 B2 | 11/2003 | Boyer, II et al. |
| 6,652,872 B2 | 11/2003 | Nevo et al. |
| 6,662,805 B2 | 12/2003 | Frondoza et al. |
| 6,666,892 B2 | 12/2003 | Hiles et al. |
| 6,686,184 B1 | 2/2004 | Anderson et al. |
| 6,689,747 B2 | 2/2004 | Filvaroff et al. |
| 6,696,073 B2 | 2/2004 | Boyce et al. |
| 6,712,851 B1 | 3/2004 | Lemperle et al. |
| 6,727,224 B1 | 4/2004 | Zhang et al. |
| RE38,522 E | 5/2004 | Gertzman et al. |
| 6,730,314 B2 | 5/2004 | Jeschke et al. |
| 6,734,018 B2 | 5/2004 | Wolfinbarger, Jr. et al. |
| 6,743,232 B2 | 6/2004 | Overaker et al. |
| 6,752,834 B2 | 6/2004 | Geistlich et al. |
| 6,761,739 B2 | 7/2004 | Shepard |
| 6,761,887 B1 | 7/2004 | Kavalkovich et al. |
| 6,767,369 B2 | 7/2004 | Boyer, II et al. |
| 6,776,800 B2 | 8/2004 | Boyer, II et al. |
| 6,783,712 B2 | 8/2004 | Slivka et al. |
| 6,808,585 B2 | 10/2004 | Boyce et al. |
| 6,815,416 B2 | 11/2004 | Carney et al. |
| 6,838,440 B2 | 1/2005 | Stiles |
| 6,841,150 B2 | 1/2005 | Halvorsen et al. |
| 6,849,255 B2 | 2/2005 | Gazit et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,858,042 B2 | 2/2005 | Nadler et al. |
| 6,866,668 B2 | 3/2005 | Giannetti et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,902,578 B1 | 6/2005 | Anderson et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,933,328 B2 | 8/2005 | Schacht |
| 6,949,252 B2 | 9/2005 | Mizuno et al. |
| 6,989,034 B2 | 1/2006 | Hammer et al. |
| 6,995,013 B2 | 2/2006 | Connelly et al. |
| 7,009,039 B2 | 3/2006 | Yayon et al. |
| 7,018,416 B2 | 3/2006 | Hanson et al. |
| 7,033,587 B2 | 4/2006 | Halvorsen et al. |
| 7,041,641 B2 | 5/2006 | Rueger et al. |
| 7,044,968 B1 | 5/2006 | Yaccarino, III et al. |
| 7,045,141 B2 | 5/2006 | Merboth et al. |
| 7,048,750 B2 | 5/2006 | Vibe-Hansen et al. |
| 7,048,762 B1 | 5/2006 | Sander et al. |
| 7,048,765 B1 | 5/2006 | Grooms et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| 7,087,227 B2 | 8/2006 | Adkisson |
| 7,108,721 B2 | 9/2006 | Huckle et al. |
| RE39,321 E | 10/2006 | MacPhee et al. |
| 7,115,146 B2 | 10/2006 | Boyer, II et al. |
| 7,125,423 B2 | 10/2006 | Hazebrouck |
| 7,132,110 B2 | 11/2006 | Kay et al. |
| 7,137,989 B2 | 11/2006 | Asculai et al. |

| | | |
|---|---|---|
| 7,141,072 B2 | 11/2006 | Geistlich et al. |
| 7,156,880 B2 | 1/2007 | Evans et al. |
| 7,157,428 B2 | 1/2007 | Kusanagi et al. |
| 7,163,563 B2 | 1/2007 | Schwartz et al. |
| 7,166,133 B2 | 1/2007 | Evans et al. |
| 7,179,299 B2 | 2/2007 | Edwards et al. |
| 7,182,781 B1 | 2/2007 | Bianchi et al. |
| RE39,587 E | 4/2007 | Gertzman et al. |
| 7,201,917 B2 | 4/2007 | Malaviya et al. |
| 7,217,294 B2 | 5/2007 | Kusanagi et al. |
| 7,220,558 B2 | 5/2007 | Luyten et al. |
| 7,241,316 B2 | 7/2007 | Evans et al. |
| 7,252,987 B2 | 8/2007 | Bachalo et al. |
| 7,264,634 B2 | 9/2007 | Schmieding |
| 7,273,756 B2 | 9/2007 | Adkisson et al. |
| 7,288,406 B2 | 10/2007 | Bogin et al. |
| 7,291,169 B2 | 11/2007 | Hodorek |
| 7,297,161 B2 | 11/2007 | Fell |
| 7,316,822 B2 | 1/2008 | Binette et al. |
| 7,323,011 B2 | 1/2008 | Shepard et al. |
| 7,323,445 B2 | 1/2008 | Zhang et al. |
| 7,335,508 B2 | 2/2008 | Yayon et al. |
| 7,338,492 B2 | 3/2008 | Singhatat |
| 7,338,524 B2 | 3/2008 | Fell et al. |
| 7,358,284 B2 | 4/2008 | Griffey et al. |
| 7,361,195 B2 | 4/2008 | Schwartz et al. |
| 7,365,051 B2 | 4/2008 | Paulista et al. |
| 7,371,400 B2 | 5/2008 | Borenstein et al. |
| 7,468,075 B2 | 12/2008 | Lang et al. |
| 7,468,192 B2 | 12/2008 | Mizuno et al. |
| 7,476,257 B2 | 1/2009 | Sah et al. |
| 7,479,160 B2 | 1/2009 | Branch et al. |
| 7,485,310 B2 | 2/2009 | Luyten et al. |
| 7,488,348 B2 | 2/2009 | Truncale et al. |
| 7,513,910 B2 | 4/2009 | Buskirk et al. |
| 7,531,000 B2 | 5/2009 | Hodorek |
| 7,537,617 B2 | 5/2009 | Bindsell et al. |
| 7,537,780 B2 | 5/2009 | Mizuno et al. |
| 7,548,865 B2 | 6/2009 | Schmieding |
| 7,550,007 B2 | 6/2009 | Malinin |
| 7,563,455 B2 | 7/2009 | McKay |
| 7,563,769 B2 | 7/2009 | Bogin et al. |
| 7,601,173 B2 | 10/2009 | Messerli et al. |
| 7,608,113 B2 | 10/2009 | Boyer, II et al. |
| 7,621,963 B2 | 11/2009 | Simon et al. |
| 7,622,438 B1 | 11/2009 | Lazarov et al. |
| 7,622,562 B2 | 11/2009 | Thorne et al. |
| 7,628,851 B2 | 12/2009 | Armitage et al. |
| 7,632,311 B2 | 12/2009 | Seedhom et al. |
| 7,638,486 B2 | 12/2009 | Lazarov et al. |
| 7,642,092 B2 | 1/2010 | Maor |
| 7,648,700 B2 | 1/2010 | Vignery et al. |
| 7,648,965 B2 | 1/2010 | Vignery et al. |
| 7,658,768 B2 | 2/2010 | Miller et al. |
| 7,662,184 B2 | 2/2010 | Edwards et al. |
| 7,666,230 B2 | 2/2010 | Orban et al. |
| RE41,286 E | 4/2010 | Atkinson et al. |
| 7,824,701 B2 | 11/2010 | Binette et al. |
| 7,837,740 B2 | 11/2010 | Semler et al. |
| 7,875,296 B2 | 1/2011 | Binette et al. |
| RE42,208 E | 3/2011 | Truncale et al. |
| 7,901,457 B2 | 3/2011 | Truncale et al. |
| 7,901,461 B2 | 3/2011 | Harmon et al. |
| 2001/0005592 A1 | 6/2001 | Bhatnagar et al. |
| 2001/0006634 A1 | 7/2001 | Zaleske et al. |
| 2001/0010023 A1 | 7/2001 | Schwartz et al. |
| 2001/0011131 A1 | 8/2001 | Luyten et al. |
| 2001/0016646 A1 | 8/2001 | Rueger et al. |
| 2001/0018619 A1 | 8/2001 | Enzerink et al. |
| 2001/0020188 A1 | 9/2001 | Sander |
| 2001/0021875 A1 | 9/2001 | Enzerink et al. |
| 2001/0031254 A1 | 10/2001 | Bianchi et al. |
| 2001/0039457 A1 | 11/2001 | Boyer, II et al. |
| 2001/0039458 A1 | 11/2001 | Boyer, II et al. |
| 2001/0043940 A1 | 11/2001 | Boyce et al. |
| 2001/0051834 A1 | 12/2001 | Frondoza et al. |
| 2002/0009805 A1 | 1/2002 | Nevo et al. |
| 2002/0016592 A1 | 2/2002 | Branch et al. |
| 2002/0035401 A1 | 3/2002 | Boyce et al. |
| 2002/0042373 A1 | 4/2002 | Carney et al. |
| 2002/0045940 A1 | 4/2002 | Giannetti et al. |
| 2002/0055783 A1 | 5/2002 | Tallarida et al. |
| 2002/0072806 A1 | 6/2002 | Buskirk et al. |
| 2002/0082704 A1 | 6/2002 | Cerundolo |
| 2002/0099448 A1 | 7/2002 | Hiles et al. |
| 2002/0106393 A1 | 8/2002 | Bianchi et al. |
| 2002/0111695 A1 | 8/2002 | Kandel |
| 2002/0120274 A1 | 8/2002 | Overaker et al. |
| 2002/0138143 A1 | 9/2002 | Grooms et al. |
| 2002/0177224 A1 | 11/2002 | Madry et al. |
| 2002/0192263 A1 | 12/2002 | Merboth et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0039695 A1 | 2/2003 | Geistlich et al. |
| 2003/0040113 A1 | 2/2003 | Mizuno et al. |
| 2003/0044444 A1 | 3/2003 | Malaviya et al. |
| 2003/0049299 A1 | 3/2003 | Malaviya et al. |
| 2003/0050709 A1 | 3/2003 | Noth et al. |
| 2003/0055502 A1 | 3/2003 | Lang et al. |
| 2003/0077821 A1 | 4/2003 | Sah et al. |
| 2003/0078617 A1 | 4/2003 | Schwartz et al. |
| 2003/0099620 A1 | 5/2003 | Zaleske et al. |
| 2003/0139591 A1 | 7/2003 | Luyten et al. |
| 2003/0144743 A1 | 7/2003 | Edwards et al. |
| 2003/0229400 A1 | 12/2003 | Masuda et al. |
| 2003/0236573 A1 | 12/2003 | Evans et al. |
| 2004/0024457 A1 | 2/2004 | Boyce et al. |
| 2004/0028717 A1 | 2/2004 | Sittinger et al. |
| 2004/0033212 A1 | 2/2004 | Thomson et al. |
| 2004/0039447 A1 | 2/2004 | Simon et al. |
| 2004/0044408 A1 | 3/2004 | Hungerford et al. |
| 2004/0062753 A1 | 4/2004 | Rezania et al. |
| 2004/0078078 A1 | 4/2004 | Shepard |
| 2004/0078090 A1 | 4/2004 | Binette et al. |
| 2004/0102850 A1 | 5/2004 | Shepard |
| 2004/0107003 A1* | 6/2004 | Boyer et al. ............... 623/23.63 |
| 2004/0127987 A1 | 7/2004 | Evans et al. |
| 2004/0134502 A1 | 7/2004 | Mizuno et al. |
| 2004/0138748 A1 | 7/2004 | Boyer, II et al. |
| 2004/0143344 A1 | 7/2004 | Malaviya et al. |
| 2004/0151705 A1 | 8/2004 | Mizuno et al. |
| 2004/0166169 A1 | 8/2004 | Malaviya et al. |
| 2004/0170610 A1 | 9/2004 | Slavin et al. |
| 2004/0175826 A1 | 9/2004 | Maor |
| 2004/0192605 A1 | 9/2004 | Zhang et al. |
| 2004/0193268 A1 | 9/2004 | Hazebrouck |
| 2004/0197311 A1 | 10/2004 | Brekke et al. |
| 2004/0197373 A1 | 10/2004 | Gertzman et al. |
| 2004/0219182 A1 | 11/2004 | Gomes et al. |
| 2004/0220574 A1 | 11/2004 | Pelo et al. |
| 2004/0230303 A1* | 11/2004 | Gomes et al. ............... 623/16.11 |
| 2004/0241203 A1 | 12/2004 | Shakesheff et al. |
| 2004/0243242 A1 | 12/2004 | Sybert et al. |
| 2005/0004672 A1 | 1/2005 | Pafford et al. |
| 2005/0027307 A1 | 2/2005 | Schwartz et al. |
| 2005/0043814 A1 | 2/2005 | Kusanagi et al. |
| 2005/0064042 A1 | 3/2005 | Vunjak-Novakovia et al. |
| 2005/0074476 A1 | 4/2005 | Gendler et al. |
| 2005/0074481 A1 | 4/2005 | Brekke et al. |
| 2005/0089544 A1 | 4/2005 | Khouri et al. |
| 2005/0101957 A1 | 5/2005 | Buskirk et al. |
| 2005/0112761 A1 | 5/2005 | Halvorsen et al. |
| 2005/0125077 A1 | 6/2005 | Harmon et al. |
| 2005/0129668 A1 | 6/2005 | Giannetti et al. |
| 2005/0152882 A1 | 7/2005 | Kizer et al. |
| 2005/0159820 A1 | 7/2005 | Yoshikawa et al. |
| 2005/0159822 A1 | 7/2005 | Griffey et al. |
| 2005/0196460 A1 | 9/2005 | Malinin |
| 2005/0209705 A1 | 9/2005 | Niederauer et al. |
| 2005/0222687 A1 | 10/2005 | Vunjak-Novakovia et al. |
| 2005/0228498 A1 | 10/2005 | Andres |
| 2005/0240281 A1 | 10/2005 | Slivka et al. |
| 2005/0251268 A1 | 11/2005 | Truncale |

| | | |
|---|---|---|
| 2005/0260612 A1 | 11/2005 | Padmini et al. |
| 2005/0261681 A9 | 11/2005 | Branch et al. |
| 2005/0261767 A1 | 11/2005 | Anderson et al. |
| 2005/0288796 A1 | 12/2005 | Awad et al. |
| 2006/0030948 A1 | 2/2006 | Manrique et al. |
| 2006/0060209 A1 | 3/2006 | Shepard |
| 2006/0099234 A1 | 5/2006 | Winkler |
| 2006/0111778 A1 | 5/2006 | Michalow |
| 2006/0167483 A1 | 7/2006 | Asculai et al. |
| 2006/0178748 A1 | 8/2006 | Dinger, III et al. |
| 2006/0200166 A1 | 9/2006 | Hanson et al. |
| 2006/0210643 A1 | 9/2006 | Truncale et al. |
| 2006/0216323 A1 | 9/2006 | Knaack et al. |
| 2006/0216822 A1 | 9/2006 | Mizuno et al. |
| 2006/0235534 A1 | 10/2006 | Gertzman et al. |
| 2006/0247790 A1 | 11/2006 | McKay |
| 2006/0247791 A1 | 11/2006 | McKay et al. |
| 2006/0251631 A1 | 11/2006 | Adkisson, IV et al. |
| 2006/0276907 A1 | 12/2006 | Boyer, II et al. |
| 2006/0293757 A1 | 12/2006 | McKay et al. |
| 2007/0009610 A1 | 1/2007 | Syring |
| 2007/0014867 A1 | 1/2007 | Kusanagi et al. |
| 2007/0026030 A1 | 2/2007 | Gill et al. |
| 2007/0036834 A1 | 2/2007 | Pauletti et al. |
| 2007/0041950 A1 | 2/2007 | Leatherbury et al. |
| 2007/0055377 A1 | 3/2007 | Hanson et al. |
| 2007/0065943 A1 | 3/2007 | Smith et al. |
| 2007/0067032 A1 | 3/2007 | Felt et al. |
| 2007/0083266 A1 | 4/2007 | Lang |
| 2007/0093896 A1 | 4/2007 | Malinin |
| 2007/0093912 A1 | 4/2007 | Borden |
| 2007/0098759 A1 | 5/2007 | Malinin |
| 2007/0100450 A1 | 5/2007 | Hodorek |
| 2007/0113951 A1 | 5/2007 | Huang |
| 2007/0128155 A1 | 6/2007 | Seyedin |
| 2007/0134291 A1 | 6/2007 | Ting |
| 2007/0135917 A1 | 6/2007 | Malinin |
| 2007/0135918 A1 | 6/2007 | Malinin |
| 2007/0135928 A1 | 6/2007 | Malinin |
| 2007/0148242 A1 | 6/2007 | Vilei et al. |
| 2007/0162121 A1 | 7/2007 | Tarrant et al. |
| 2007/0168030 A1 | 7/2007 | Edwards et al. |
| 2007/0172506 A1 | 7/2007 | Nycz et al. |
| 2007/0179607 A1 | 8/2007 | Hodorek et al. |
| 2007/0185585 A1* | 8/2007 | Bracy et al. ............... 623/23.63 |
| 2007/0276506 A1 | 11/2007 | Troxel |
| 2007/0299517 A1 | 12/2007 | Davisson |
| 2007/0299519 A1 | 12/2007 | Schmieding |
| 2008/0015709 A1 | 1/2008 | Evans et al. |
| 2008/0027546 A1 | 1/2008 | Semler et al. |
| 2008/0031915 A1 | 2/2008 | Becerra Ratia et al. |
| 2008/0038314 A1 | 2/2008 | Hunziker |
| 2008/0039939 A1 | 2/2008 | Iwamoto et al. |
| 2008/0039954 A1 | 2/2008 | Long et al. |
| 2008/0039955 A1 | 2/2008 | Hunziker |
| 2008/0051889 A1 | 2/2008 | Hodorek |
| 2008/0058953 A1 | 3/2008 | Scarborough |
| 2008/0065210 A1 | 3/2008 | McKay |
| 2008/0077251 A1 | 3/2008 | Chen et al. |
| 2008/0119947 A1 | 5/2008 | Huckle et al. |
| 2008/0125863 A1 | 5/2008 | McKay |
| 2008/0125868 A1 | 5/2008 | Branemark |
| 2008/0133008 A1 | 6/2008 | Truncale et al. |
| 2008/0138414 A1 | 6/2008 | Huckle et al. |
| 2008/0153157 A1 | 6/2008 | Yao et al. |
| 2008/0154372 A1 | 6/2008 | Peckham |
| 2008/0167716 A1 | 7/2008 | Schwartz et al. |
| 2008/0183300 A1 | 7/2008 | Seedhom et al. |
| 2008/0220044 A1 | 9/2008 | Semler et al. |
| 2008/0249632 A1 | 10/2008 | Stone et al. |
| 2008/0255676 A1 | 10/2008 | Semler et al. |
| 2008/0274157 A1 | 11/2008 | Vunjak-Novakovic et al. |
| 2008/0294270 A1 | 11/2008 | Yao et al. |
| 2008/0305145 A1 | 12/2008 | Shelby et al. |
| 2009/0024224 A1 | 1/2009 | Chen et al. |
| 2009/0043389 A1 | 2/2009 | Vunjak-Novakovic et al. |
| 2009/0069901 A1 | 3/2009 | Truncale et al. |
| 2009/0069904 A1 | 3/2009 | Picha |
| 2009/0076624 A1 | 3/2009 | Rahaman et al. |
| 2009/0099661 A1 | 4/2009 | Bhattacharya et al. |
| 2009/0117652 A1 | 5/2009 | Luyten et al. |
| 2009/0131986 A1 | 5/2009 | Lee et al. |
| 2009/0149893 A1 | 6/2009 | Semler et al. |
| 2009/0210057 A1 | 8/2009 | Liao et al. |
| 2009/0226523 A1 | 9/2009 | Behnam et al. |
| 2009/0248592 A1 | 10/2009 | Schmieding |
| 2009/0280179 A1 | 11/2009 | Neumann et al. |
| 2009/0299475 A1 | 12/2009 | Yamamoto et al. |
| 2009/0312805 A1 | 12/2009 | Lang et al. |
| 2009/0312842 A1 | 12/2009 | Bursac et al. |
| 2009/0319051 A9 | 12/2009 | Nycz et al. |
| 2009/0324722 A1 | 12/2009 | Elisseeff |
| 2010/0021521 A1 | 1/2010 | Xu et al. |
| 2010/0036492 A1 | 2/2010 | Hung et al. |
| 2010/0036503 A1 | 2/2010 | Chen et al. |
| 2010/0322994 A1 | 12/2010 | Kizer et al. |
| 2011/0052705 A1 | 3/2011 | Malinin |
| 2011/0070271 A1 | 3/2011 | Truncale et al. |
| 2011/0104242 A1 | 5/2011 | Malinin |
| 2012/0009224 A1 | 1/2012 | Kizer et al. |
| 2012/0009270 A1 | 1/2012 | Kizer et al. |

FOREIGN PATENT DOCUMENTS

| | | |
|---|---|---|
| EP | 0762903 A1 | 12/1995 |
| EP | 0517030 B1 | 9/1996 |
| EP | 0739631 A2 | 10/1996 |
| EP | 0784985 A1 | 7/1997 |
| EP | 0739631 A3 | 5/1998 |
| EP | 0968012 A1 | 9/1998 |
| EP | 1237511 A1 | 6/2001 |
| EP | 1127581 A1 | 8/2001 |
| EP | 1181908 A1 | 2/2002 |
| EP | 1234552 A1 | 8/2002 |
| EP | 1234555 A2 | 8/2002 |
| EP | 0739631 B1 | 3/2003 |
| EP | 0762903 B1 | 9/2003 |
| EP | 1181908 B1 | 12/2003 |
| EP | 1384452 A1 | 1/2004 |
| EP | 1234555 A3 | 6/2004 |
| EP | 1237511 B1 | 9/2004 |
| EP | 1618178 A1 | 11/2004 |
| EP | 1127581 B1 | 6/2005 |
| EP | 1561481 A2 | 8/2005 |
| EP | 1234552 B1 | 8/2006 |
| EP | 0968012 B1 | 9/2006 |
| EP | 1719463 A1 | 11/2006 |
| EP | 1719531 A2 | 11/2006 |
| EP | 1719532 A2 | 11/2006 |
| EP | 1234555 B1 | 2/2007 |
| EP | 0762903 B2 | 8/2007 |
| EP | 1740121 A2 | 10/2007 |
| EP | 1537883 B1 | 4/2008 |
| EP | 1618178 B1 | 7/2008 |
| EP | 1416880 B1 | 3/2011 |
| GB | 2102811 A1 | 2/1983 |
| SU | 1454423 A1 | 1/1989 |
| WO | WO 84/04880 A1 | 12/1984 |
| WO | 90/01342 A1 | 2/1990 |
| WO | 93/16739 A1 | 9/1993 |
| WO | WO 94/03584 A1 | 2/1994 |
| WO | 95/25748 A1 | 9/1995 |
| WO | WO 95/33502 A1 | 12/1995 |
| WO | 96/24310 A1 | 8/1996 |
| WO | 97/37613 A1 | 10/1997 |
| WO | WO 98/14222 A1 | 4/1998 |
| WO | 98/34569 A1 | 8/1998 |
| WO | WO 98/41246 A2 | 9/1998 |
| WO | 98-43686 A1 | 10/1998 |
| WO | 99/08728 A1 | 2/1999 |
| WO | WO 99/09914 A1 | 3/1999 |
| WO | WO 99/11298 A2 | 3/1999 |
| WO | 99/15209 A1 | 4/1999 |
| WO | WO 99/21497 A1 | 5/1999 |
| WO | WO 99/22747 A1 | 5/1999 |
| WO | WO 99/48541 A1 | 9/1999 |
| WO | WO 99/52572 A1 | 10/1999 |
| WO | 99/56797 A1 | 11/1999 |
| WO | WO 00/40177 A1 | 7/2000 |

| | | |
|---|---|---|
| WO | 00/47114 A1 | 8/2000 |
| WO | 00/72782 A1 | 12/2000 |
| WO | 01/07595 A2 | 2/2001 |
| WO | 01/38357 A2 | 5/2001 |
| WO | 01/39788 A2 | 6/2001 |
| WO | 01/46416 A1 | 6/2001 |
| WO | WO 01/43667 A1 | 6/2001 |
| WO | 02/18546 A2 | 3/2002 |
| WO | 02/22779 A2 | 3/2002 |
| WO | 02/36732 A2 | 5/2002 |
| WO | WO 02/058484 A2 | 8/2002 |
| WO | 02/077199 A2 | 10/2002 |
| WO | 02/095019 A1 | 11/2002 |
| WO | 03/007873 A2 | 1/2003 |
| WO | WO 03/007805 A2 | 1/2003 |
| WO | WO 03/007879 A2 | 1/2003 |
| WO | 03/012053 A2 | 2/2003 |
| WO | WO 03/007879 A3 | 5/2003 |
| WO | 03/079985 A2 | 10/2003 |
| WO | 03/087160 A1 | 10/2003 |
| WO | 03/094835 A2 | 11/2003 |
| WO | WO 03/007805 A3 | 2/2004 |
| WO | 2004/067704 A2 | 8/2004 |
| WO | 2004/069298 A1 | 8/2004 |
| WO | WO 2004/075940 A1 | 9/2004 |
| WO | WO 2004/096983 A2 | 11/2004 |
| WO | WO 2004/103224 A1 | 12/2004 |
| WO | 2005058207 A1 | 6/2005 |
| WO | WO 2005/110278 A2 | 11/2005 |
| WO | WO 2004/096983 A3 | 12/2005 |
| WO | 2006/036681 A2 | 4/2006 |
| WO | WO 2006/042311 A2 | 4/2006 |
| WO | 2006/050213 A2 | 5/2006 |
| WO | WO 2005/110278 A3 | 8/2006 |
| WO | 2002/036732 A3 | 9/2006 |
| WO | 2006/113586 A2 | 10/2006 |
| WO | WO 2006/042311 A3 | 11/2006 |
| WO | 2003/094835 A3 | 12/2006 |
| WO | WO 2007/024238 A1 | 3/2007 |
| WO | 2006/113586 A3 | 9/2007 |
| WO | 2008/013763 A2 | 1/2008 |
| WO | WO 2008/021127 A2 | 2/2008 |
| WO | 2008/038287 A2 | 4/2008 |
| WO | 2008/013763 A3 | 6/2008 |
| WO | 2008/081463 A2 | 7/2008 |
| WO | 2008/038287 A3 | 9/2008 |
| WO | WO 2008/106254 A2 | 9/2008 |
| WO | WO 2009/076164 A2 | 6/2009 |
| WO | WO 2009/111069 A1 | 9/2009 |
| WO | 2009/155232 A1 | 12/2009 |

OTHER PUBLICATIONS

Aston et al., "Repair of Articular Surfaces by Allografts of Articular and Growth-Plate Cartilage," Journal of Bone and Joint Surgery, Jan. 1985, vol. 68-B, No. 1, pp. 29-35.

Hoffman, "Hydrogels for Biomedical Applications", Advanced Drug Delivery Reviews, 2002, vol. 43, pp. 3-12.

Dahlberg et al., "Demineralized Allogeneic Bone Matrix for Cartilage Repair", Journal of Orthopaedic Research, 1991, vol. 9, pp. 11-19.

Lu et al., "Minced Cartilage without Cell Culture Serves as an Effective Intraoperative Cell Source for Cartilage Repair", Journal of Orthopaedic Research, Jun. 2006, vol. 24, pp. 1261-1270.

Stone et al., "Articular Cartilage Paste Grafting to Full-Thickness Articular Cartilage Knee Joint Lesions: A 2- to 12-Year Follow-up", Arthroscopy: The Journal of Arthoscopic and Related Surgery, Mar. 2006, vol. 22, No. 3, pp. 291-299.

Newman, "Articular Cartilage Repair", American Journal of Sports Medicine, 1998, vol. 26, No. 2, pp. 309-324.

Brittberg et al., "Treatment of Deep Cartilage Defects in the Knee with Autologous Chondrocyte Transplantation", New England Journal of Medicine, Oct. 6, 1994, vol. 331, No. 14, pp. 889-895.

Nixon et al., "Enhanced Repair of Extensive Articular Defects by Insulin-like Growth Factor-I-Laden Fibrin Composites", Journal of Orthopaedic Research, 1999; 17:475-487.

International Cartilage Repair Society, "Cartilage Injury Evaluation Package", www.cartilage.org, 2000.

Richardson et al., "Repair of Human Articular Cartilage After Implantation of Autologous Chondrocytes", Journal of Bone and Joint Surgery [Br], 1999; 81-B:1064-1068.

Brittberg et al., "Autologous Chondrocytes Used for Articular Cartilage Repair: An Update", Clinical Orthopaedics and Related Research, 2001; No. 391 Suppl: S337-S348.

Peterson et al., "Two- to 9-year Outcome After Autologous Chondrocyte Transplantation of the Knee", Clinical Orthopaedics and Related Research, 2000; No. 374: 212-234.

Peterson et al., "Autologous Chondrocyte Transplantation: Biomechanics and Long-term Durability", American Journal of Sports Medicine, 2002, vol. 30, No. 1, pp. 2-12.

Messner et al., "Cartilage Repair: A Critical Review", Acta Orthopaedica Scandinavica,1996, vol. 67, No. 5, pp. 523-529.

Messner et al., "The Long-term Prognosis for Severe Damage to Weight-bearing Cartilage in the Knee: A 14-year Clinical and Radiographic Follow-up in 28 Young Athletes", Acta Orthopaedica Scandinavica, 1996, vol. 67, No. 2, pp. 165-168.

Buckwalter et al., "Articular Cartilage: Degeneration and Osteoarthritis, Repair, Regeneration, and Transplantation", AAOS Instructional Course Lectures, 1998; 47:487-504.

Breinan et al., "Effect of Cultured Autologous Chondrocytes on Repair of Chondral Defects in a Canine Model", Journal of Bone and Joint Surgery [Am], Oct. 1997; vol. 79-A, No. 10, 1439-1451.

Breinan et al., "Autologous Chondrocyte Implantation in a Canine Model: Change in Composition of Reparative Tissue with Time", Journal of Orthopaedic Research, 2001; 19:482-492.

Brittberg et al., "Rabbit Articular Cartilage Defects Treated with Autologous Cultured Chondrocytes", Clinical Orthopaedics and Related Research, 1996; 326:270-283.

Nehrer et al., "Chondrocyte-seeded Collagen Matrices Implanted in a Chondral Defect in a Canine Model", Biomaterials, 1998; 19:2313-2328.

Vunjak-Novakovic et al., "Bioreactor Cultivation Conditions Modulate the Composition and Mechanical Properties of Tissue-Engineered Cartilage", Journal of Orthopaedic Research, 1999; 17:130-138.

Bursac, "Collagen Network Contributions to Structure-Function Relationships in Cartilaginous Tissues in Compression" (Dissertation), Boston University College of Engineering, 2002.

Gooch et al., "IGF-I and Mechanical Environment Interact to Modulate Engineered Cartilage Development", Biochemical and Biophysical Research Communications, 2001; 286:909-915.

Pei et al., "Growth Factors for Sequential Cellular De- and Re-differentiation in Tissue Engineering", Biochemical and Biophysical Research Communications, 2002; 294:149-154.

Obradovic et al., "Integration of Engineered Cartilage", Journal of Orthopaedic Research, 19:1089-1097, 2001.

Schaefer et al., "Tissue Engineered Composites for the Repair of Large Osteochondral Defects", Arthritis & Rheumatism, 46(9): 2524-2534 (2002).

Pei et al., "Bioreactors Mediate the Effectiveness of Tissue Engineering Scaffolds", The FASEB Journal, 16:1691-1694, published online (Aug. 7, 2002), 10.1096/fj.02-0083fje.

Madry et al., "Gene Transfer of a Human Insulin-like Growth Factor I cDNA Enhances Tissue Engineering of Cartilage", Human Gene Therapy, 13: 1621-1630 (Sep. 1, 2002).

Pearson et al. (eds.), American Association of Tissue Banks, Standards for Tissue Banking, 2008 (12th ed.), pp. 53-56, 86-88.

Osteo Sponge product information, Bacterin International Inc., May 2005.

Nolan et at., "Living Bone Grafts", BMJ, vol. 304, Jun. 13, 1992, pp. 1520 and 1521.

Stone et al., "One-Step American Technique of Articular Cartilage Paste Grafting to Traumatic and Arthritic Defects in the Knee Joint (2-7 Years Follow-Up)", downloaded from http:web.archive.org/web/20041205005845/http://www.stoneclinic.com/onestep.thm; published Dec. 5, 2004.

Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755-761.

Nettles et al., "In Situ Crosslinkable Hyaluronan for Articular Cartilage Repair", 50th Annual Meeting of the Orthopaedic Research Society, Paper No. 0202.

Nettles et al., "Photocrosslinkable Hyaluronan as a Scaffold for Articular Cartilage Repair", Annals of Biomedical Engineering, vol. 32, No. 3, Mar. 2004, pp. 391-397.

Peretti et al., "Cell-Based Bonding of Articular Cartilage: An Extended Study", Journal of Biomedical Materials Research, 64A, 2003, pp. 517-524.

Bugbee, "Fresh Osteochondral Allografting", Operative Techniques in Sports Medicine, Apr. 2000, vol. 8, No. 2, pp. 158-162.

Verbruggen et al., "Repair Function in Organ Cultured Human Cartilage. Replacement of Enzymatically Removed Proteoglycans During Longterm Organ Culture", The Journal of Rheumatology, 12:4, (1985), pp. 665-674.

Peretti et al., "Cell-based Tissue-Engineered Allogeneic Implant for Cartilage Repair" Tissue Engineering, 2000, vol. 6. No. 5, pp. 567-576.

Jackson et al., "Cartilage Substitute: Overview of Basic Science & Treatment Options", Journal of American Academy of Orthopaedic Surgeons, vol. 9, Jan./Feb. 2001, pp. 37-52.

Glowacki, Julie, "Engineered Cartilage, Bone, Joints and Menisci—Potential for Temporomandibular Joint Reconstruction", Cells tissues Organs, vol. 169, Issue 3, 2001, pp. 302-308.

Peretti et al., "A Biomedical Analysis of an Engineered Cell-Scaffold Implant for Cartilage Repair", Annals of Plastic Surgery, 2001, vol. 46, No. 5, pp. 533-537.

Peretti et al., "Biomechanical Analysis of a Chondrocyte-Based Repair Model of Articular Cartilage", Tissue Engineering, Aug. 1, 1999, vol. 5. No. 4, pp. 317-326.

Peretti et al., "In Vitro Bonding of Pre-seeded Chondrocyte", Sport Sciences for Health, May 1, 2007, vol. 2, No. 1, pp. 29-33.

Peretti et al., "Bonding of Cartilage Matrices with Cultured Chondrocytes: An Experiential Model", Journal of Orthopedic Research, Jan. 1998, vol. 16, No. 1, pp. 89-95.

Hunziker, "Articular Cartilage Repair: Basic Science and Clinical Progress. A Review of the Current Status and Prospects", Osteoarthritis and Cartilage 2001, vol. 10, No. 6, pp. 432-463.

Chen et al., "Repair of Articular Cartilage Defects: Part I, Basic Science of Cartilage Healing", The American Journal of Orthopedics, Jan. 1999, pp. 31-33.

Chen et al., "Repair of Articular Cartilage Defects: Part II. Treatment Options", The American Journal of Orthopedics, Feb. 1999, pp. 88-96.

Buckwalter, "Articular Cartilage Injuries", Clinical Orthopaedics and Related Research, 2002, No. 402, pp. 21-37.

Nixon et al., "New Horizons in Articular Cartilage Repair", Proceedings of the Annual Convention of the AAEP, 2001, vol. 47, pp. 217-226.

Tsumaki et al. "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.

Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.

Brighton et al., "Articular Cartilage Preservation and Storage—I. Application of Tissue Culture Techniques to the Storage of Viable Articular Cartilage", Arthritis and Rheumatism, vol. 22, No. 10 (Oct. 1979), pp. 1093-1101.

Mahadev et al., "Autogenous Osteochondral Morselised Grafts for Full Thickness Osteochondral Defects in the Knee Joints of Pigs", Singapore Medical Journal, 2001, vol. 42(9), pp. 410-416.

Hunziker, "Articular Cartilage Structure in Humans and Experimental Animals", *Articular Cartilage and Osteoarthritis*, Raven Press, ed., 2001, pp. 183-199.

Girotto et al., "Tissue-specific gene expression in chondrocytes grown on three-dimensional hyaluronic acid scaffolds", Biomaterials, vol. 24 (2003), pp. 3265-3275.

Gertzman et al., "A pilot study evaluating sodium hyaluronate as a carrier for freeze-dried demineralized bone powder", Cell and Tissue Banking, vol. 2, 2001, pp. 87-94.

Diduch et al., "Joint Repair: Treatment Options for Articular Cartilage Injury" Orthopedic Technology Review (2002) 4:24-27.

Gilbert, et al., "Decellularization of Tissues and Organs", Biomaterials (2006) 27:3675-3683.

http://www.technobusiness-solutions.com/article-lyophilization1.html (published Feb. 12, 2002).

Loeser et al., "Basic Fibroblast Growth Factor Inhibits the Anabolic Activity of Insulin-like Growth Factor 1 and Osteogenic Protein 1 in Adult Human Articular Chondrocytes", Arthritis & Rheumatism, vol. 52, No. 12 (Dec. 2005), pp. 3910-3917.

Kato et al., "Fibroblast Growth Factor is an Inhibitor of Chondrocyte Terminal Differentiation", Journal of Biological Chemistry, vol. 265, No. 10 (Apr. 5, 1990) pp. 5903-5909.

Andrés et al., "A Pro-Inflammatory Signature Mediates FGF2-induced Angiogenesis", Journal of Cellular and Molecular Medicine, (Jun. 28, 2008), available at http://www.ncbi.nlm.nih.gov/pubmed/18624773.

Burger et al., "Fibroblast growth factor receptor-1 is expressed by endothelial progenitor cells", Blood, vol. 100, No. 10 (Nov. 15, 2002) 3527-35.

Baird, "Fibroblast growth factors: activities and significance of non-neurotrophin neurotrophic growth factors", Current Opinions in Neurobiology, (1994) 4:78-86.

Mazué et al., "Preclinical and Clinical Studies with Recombinant Human Basic Fibroblast Growth Factor", Annals New York Academy of Sciences, (1991) 329-340.

Aviles et al., "Testing clinical therapeutic angiogenesis using basic fibroblast growth factor (FGF-2)", British Journal of Pharmacology (2003) 140: 637-646.

Ornitz et al., "Protein Family Review: Fibroblast Growth Factors", Genome Biology (2001) 2(3): 3005.1-3005.12, http://genomebiology.com/2001/2/3/reviews/3005.1.

Non-final Office Action mailed on Oct. 5, 2005 in connection with U.S. Appl. No. 10/424,765.

U.S. Appl. No. 12/147,042, filed Jun. 26, 2008, titled Novel Glue for Cartilage Repair.

Non-final Office Action mailed on Aug. 19, 2009 in connection with U.S. Appl. No. 12/147,042.

Final Office Action mailed on Sep. 19, 2008 in connection with U.S. Appl. No. 11/081,103.

Non-final Office Action mailed on Jun. 3, 2009 in connection with U.S. Appl. No. 11/081,103.

Final Office Action mailed on Jul. 22, 2009 in connection with U.S. Appl. No. 12/010,984.

Non-final Office Action mailed on Jun. 8, 2009 in connection with U.S. Appl. No. 11/481,955.

Non-final Office Action mailed on Feb. 6, 2007 in connection with U.S. Appl. No. 10/438,883.

Non-final Office Action mailed on Nov. 12, 2008 in connection with U.S. Appl. No. 10/438,883.

Non-final Office Action mailed on May 3, 2005 in connection with U.S. Appl. No. 10/438,883.

Non-final Office Action mailed on Nov. 5, 2004 in connection with U.S. Appl. No. 10/438,883.

Non-final Office Action mailed on Jul. 2, 2009 in connection with U.S. Appl. No. 10/815,778.

Non-final Office Action mailed on Feb. 7, 2008 in connection with U.S. Appl. No. 10/815,778.

Final Office Action mailed on Nov. 13, 2008 in connection with U.S. Appl. No. 10/815,778.

Non-final Office Action mailed on May 18, 2009 in connection with U.S. Appl. No. 11/657,042.

International Search Report mailed on Nov. 1, 2004 in connection with International Patent Application No. PCT/US04/010957.

Written Opinion mailed on Nov. 1, 2004 in connection with International Patent Application No. PCT/US04/010957.

International Preliminary Report on Patentability mailed on Nov. 18, 2005 in connection with International Patent Application No. PCT/US04/010957.

International Search Report mailed on Apr. 7, 2006 in connection with International Patent Application No. PCT/US05/030610.

Written Opinion mailed on Apr. 7, 2006 in connection with International Patent Application No. PCT/US05/030610.

International Preliminary Report on Patentability mailed on Feb. 26, 2008 in connection with International Patent Application No. PCT/US05/030610.
International Search Report mailed on Sep. 21, 2006 in connection with International Patent Application No. PCT/US05/036878.
Written Opinion mailed on Sep. 21, 2006 in connection with International Patent Application No. PCT/US05/036878.
International Preliminary Report on Patentability mailed on Apr. 17, 2007 in connection with International Patent Application No. PCT/US05/036878.
International Search Report mailed on Jun. 19, 2006 in connection with International Patent Application No. PCT/US05/008798.
International Search Report mailed on Oct. 28, 2005 in connection with International Patent Application No. PCT/US04/010956.
Written Opinion mailed on Oct. 28, 2005 in connection with International Patent Application No. PCT/US04/010956.
International Preliminary Report on Patentability mailed on Nov. 18, 2005 in connection with International Patent Application No. PCT/US04/010956.
International Search Report mailed on Jun. 23, 2009 in connection with International Patent Application No. PCT/US08/051796.
Written Opinion mailed on Jun. 23, 2009 in connection with International Patent Application No. PCT/US08/051796.
International Search Report mailed on Jul. 6, 2009 in connection with International Patent Application No. PCT/US08/085522.
Written Opinion mailed on Jul. 6, 2009 in connection with International Patent Application No. PCT/US08/085522.
International Search Report mailed on Jul. 6, 2009 in connection with International Patent Application No. PCT/US09/001459.
Written Opinion mailed on Jul. 6, 2009 in connection with International Patent Application No. PCT/US09/001459.
U.S. Appl. No. 12/381,072, filed Mar. 5, 2009, titled Cancellous Constructs, Cartilage Particles and Combinations of Cancellous Constructs and Cartilage Particles.
Final Office Action mailed on Oct. 18, 2005 in connection with U.S. Appl. No. 10/438,883.
A Communication from the USPTO mailed on Oct. 9, 2007 in connection with U.S. Appl. No. 10/438,883.
The Written Opinion issued on Jun. 19, 2006 in connection with PCT/US2005/008798.
The International Preliminary Report on Patentability issued on Nov. 1, 2006 in connection with International Patent Application No. PCT/US2005/008798.
The International Preliminary Report on Patentability issued on Jul. 28, 2009 in connection with International Patent Application No. PCT/US2008/051796.
Non-final Office Action mailed on Dec. 18, 2007 in connection with U.S. Appl. No. 11/081,103.
Final Office Action mailed on Sep. 28, 2007 in connection with U.S. Appl. No. 10/960,960.
Non-final Office Action mailed on Feb. 20, 2007 in connection with U.S. Appl. No. 10/960,960.
http://www.stoneclinic.com/articularcartilagepastegrafting (listing a copyright date of 2009).
Non-final Office Action mailed on Apr. 19, 2007 in connection with U.S. Appl. No. 11/151,270.
Final Office Action mailed on Oct. 9, 2007 in connection with U.S. Appl. No. 11/151,270.
An Advisory Action mailed on Dec. 27, 2007 in connection with U.S. Appl. No. 11/151,270.
Non-final Office Action mailed on Jul. 9, 2008 in connection with U.S. Appl. No. 11/151,270.
U.S. Appl. No. 12/322,996, filed Feb. 9, 2009 titled Allograft Osteochondral Plug Combined With Cartilage Particle Mixture.
U.S. Appl. No. 12/881,988, filed Sep. 14, 2010.
U.S. Appl. No. 12/924,132, filed Sep. 21, 2010.
Temenoff et al., "Review: Tissue engineering for regeneration of articular cartilage", Biomaterials 21 (2000) pp. 431-440.
Hunziker, "Articular cartilage repair: are the intrinsic biological constraints undermining this process insuperable?", Osteoarthritis and Cartilage 7 (1999) pp. 15-28.
Communication pursuant to Article 94(3) EPC for European Patent Application No. 08 782 728.3, dated Aug. 9, 2011.

International Preliminary Report on Patentability for International Patent Application No. PCT/US2010/000108, mailed Jul. 28, 2011.
First Action Interview Pilot Program Pre-Interview Communication for U.S. Appl. No. 12/931,427, mailed Aug. 19, 2011.
Nettles et al. (Mar. 2004), "In Situ Crosslinkable Hyaluronan for Articular Cartilage Repair", 50th Annual Meeting of the Orthopaedic Research Society, Paper No. 0202.
Final Office Action for U.S. Appl. No. 11/081,103, mailed Aug. 11, 2010.
Non-final Office Action for U.S. Appl. No. 12/010,984, mailed Aug. 16, 2010.
International Search Report and Written Opinion for PCT/US2010/000108, mailed Aug. 24, 2010.
Non-final Office Action for U.S. Appl. No. 12/179,034, mailed Jun. 29, 2011.
Final Office Action for U.S. Appl. No. 12/381,072, mailed Jun. 27, 2011.
Non-final Office Action for U.S. Appl. No. 12/966,674, mailed Jul. 12, 2011.
Non-final Office Action for U.S. Appl. No. 12/924,132, mailed Jul. 18, 2011.
Cheng, et al., "Chondrogenic Differentiation of Adipose-Derived Adult Stem Cells by a Porous Scaffold Derived from Native Articular Cartilage Extracellular Matrix", Tissue Engineering: Part A, vol. 15, No. 2, (2009), pp. 231-241.
Lin et al., "The Chondrocyte: Biology and Clinical Application", Tissue Engineering, vol. 12, No. 7, (2006), pp. 1971-1984.
Umlauf et al., "Cartilage biology, pathology, and repair", Cell. Mol. Life Sci., vol. 67, (2010), pp. 4197-4211.
Yee, Cindy J. et al., (2000) Analysis of fibroblast growth factor receptor 3 S249C mutation in cervical carcinoma. Journal of the National Cancer Institute 92(22):1848-1849.
Zhang, Jiandong et al., (1991) Three-dimensional structure of human basic fibroblast growth factor, a structural homolog of interleukin 1 Beta. Proc Natl Acad Sci. USA 88(8):3446-3450.
Zhu, Hengyi et al., (1995) Glu-96 of basic fibroblast growth factor is essential for high affinity receptor binding. Journal of Biological Chemistry 270(37):21869-21874.
Zhu, Hengyi et al., (1997) Analysis of high-affinity binding determinants in the receptor binding epitope of basic fibroblast growth factor. Protein Engineering 10(4):417-421.
Carr, M. E. Jr. and Alving, B. M. (1995) Effect of fibrin structure on plasmin-mediated dissolution of plasma clots. Blood Coag. Fibrinol. 6(6):567-573.
Carr, Marcus E. (1988) Fibrin formed in plasma is composed of fibers more massive than those formed from purified fibrinogen. Thromb. Haemost. 59(3):535-539.
Cook, James L. et al., (2003) Biocompatibility of three-dimensional chondrocyte grafts in large tibial defects of rabbits. Am J Vet Res. 64(1):12-20.
Gao, Jizong et al., (2002) Repair of osteochondral defect with tissue-engineered two-phase composite material of injectable calcium phosphate and hyaluronan sponge. Tissue Engin. Part A 8(5):827-837.
Gruber, Reinhard et al., (2002) Platelets stimulate proliferation of bone cells: involvement of platelet-derived growth factor, micropartides and membranes. Clin Oral Implants Res. 13(5):529-535.
Haisch, A. et al., (2000) Preparation of a pure autologous biodegradable fibrin matrix for tissue engineering. Med Biol Eng Comput. 38(6):686-689.
Itokazu, M. et al., (1997) The sustained release of antibiotic from freeze-dried fibrin¬ antibioticcompound and efficacies in a rat model of osteomyelitis. Infection 25(6):359-363.
Sims, C. Derek et al., (1998) Tissue engineered neocartilage using plasma derived polymer substrates and chondrocytes. Plastic & Recon. Surg. 101(6):1580-1585.
"Young's Modulus." Entry on http://en.wikipedia.org. accessed Oct. 27, 2005. 3 pages.
Bradford, Marion M. (1976) A Rapid and Sensitive Method for the Quantitation of Microgram Quantities of Protein Utilizing the Principle of Protein-Dye Binding. Analytical Biochemistry 72(1¬ 2):248-254.

Matsuda et al. (1995) In Vivo Chondrogenesis in Collagen Sponge Sandwiched by Perichondrium. J. Biomater. Sci. Polymer Ed., vol. 7, No. 3, pp. 221-229.

Fujisato et al. (1996) Effect of basic fibroblast growth factor on cartilage regeneration in chondrocyte-seeded collagen sponge scaffold. Biomaterials, vol. 17, No. 2, pp. 155-162.

Non-Final Office Action mailed Apr. 15, 2010 in connection with U.S. Appl. No. 12/079,629.

Non-Final Office Action mailed Apr. 12, 2010 in connection with U.S. Appl. No. 12/191,490.

Non-Final Office Action mailed Apr. 26, 2010 in connection with U.S. Appl. No. 12/147,042.

Non-Final Office Action mailed Apr. 15, 2010 in connection with U.S. Appl. No. 11/657,042.

International Preliminary Report on Patentability for PCT/US2009/001459, mailed on May 12, 2010.

Abraham, Judith A. et al., (1986) Human Basic Fibroblast Growth Factor: Nucleotide Sequence and Genomic Organization. EMBO Journal 5(10):2523-2528.

Agrawal, Sudhir et al., (1991) Pharmacokinetics. Biodistribution, and Stability of Oligodeoxynucleotide Phosphorothioates in Mice. Proc Natl Acad Sci. USA 88(17):7595¬ 7599.

Arakawa, Tsutomu et al., (1993) Production and Characterization of an Analog of Acidic Fibroblast Growth Factor With Enhanced Stability and Biological Activity. Protein Engineering 6(5):541-546.

Bailly, Karine et al., (2000) Uncoupling of cell proliferation and differentiation activities of basic fibroblast growth factor. FASEB Journal 14(2):333-343.

Bange, Johannes et al., (2002) Cancer progression and tumor cell motility are associated with the FGFR4 Arg388 allele. Cancer Research 62(3):840-846.

Bork, Peer (2000) Powers and pitfalls in sequence analysis: The 70% hurdle. Genome Res. 10(4):398-400.

Bork, Peer and Bairoch, Amnon (1996) Go hunting in sequence databases but watch out for the traps. Trends in Genetics 12(10):425-427.

Brenner, Steven E. (1999) Errors in genome annotation. Trends in Genetics 15(4):132¬ 133.

Cappellen, David et al., (1999) Frequent activating mutations of FGFR3 in human bladder and cervix carcinomas. Nature Genetics 23(1):18-20.

Chusho, Hideki et al., (2001) Dwarfism and early death in mice lacking C-type Natriuretic Peptide. Proc Natl Acad Sci. 98(7):4016-4021.

Coughlin, Shaun R. et al., (1988) Acidic and basic fibroblast growth factors stimulate tyrosine kinase activity in vivo. J Biol Chem. 263(2):988-993.

Dell'Accio, Francesco et al., (2001) Molecular markers predictive of the capacity of expanded human articular chondrocytes to form stable cartilage in vivo, Arthritis Rheum. 44(7):1608-19.

Doerks, Tobias et al., (1998) Protein annotation: detective work for function prediction. Trends Genet. 14(6):248-250 .

Dvorakova, Dana et al., (2001) Changes in the expression of FGFR3 in patients with chronic myeloid leukaemia receiving transplants of allogeneic peripheral blood stem cells_British Journal Haematology 13(3):832-835.

Eriksson, A. Elisabeth et al., (1991) Three-dimensional structure of human basic fibroblast growth factor. Proc. Natl. Acad. Sci. USA 88:3441-3445 (XP002936511).

Ezzat Shereen et al., (2002) Targeted expression of a Human pituitary tumor-derived isoform of FGF Receptor-4 Recapitulates Pituitary Tumorigenesis. Journal of Clinical Investigation 109(1):69-77.

Faham, Salem et al., (1998) Diversity does make a difference: fibroblast growth factor-Heparin interactions. Curr Opin Struct Biol 8(5):578-586.

Fingl, Edward and Woodbury, Dixon M.(1975) General Principles. In: The Pharmacological Basis of Therapeutics. Fifth edition. Goodman, Louis S. and Gilman, Alfred editors. See also table of contents.

Gargiulo, B. J. et al., (2002) Phenotypic modulation of human articular chondrocytes by bistratene A. Eur Cell Mater. 3:9-18.

Givol, David and Yayon, Avner (1992) Complexity of FGF receptors: genetic basis for structural diversity and functional specificity FASEB J. 6(15):3362-3369.

Hecht, H. J. et al., (2000) Structure of fibroblast growth factor 9 shows a symmetric dimmer with unique receptor- and heparin-binding interfaces. Acta Cryst. D57:378-384.

Johnson, Daniel E. and Williams, Lewis T. (1993) Structural and functional diversity in the FGF receptor multigene family. Adv Cancer Res. 60:1-41.

Kirikoshi, Hiroyuki et al., (2000) Molecular cloning and characterization of Human FGF-20 on chromosome 8p21.3-p22. Biochem Biophys Res Commun. 274(2):337-343.

Kuroda, S. et al., (1999) Anabolic effect of aminoterminally truncated Fibroblast Growth Factor 4 (FGF4) on bone. Bone 25:(4)431-437.

Nakatake, Yuhki et al., (2001) Identification of a novel fibroblast growth factor. FGF-22, preferentially expressed in the inner root sheath of the hair follicle. Biochim Biophys Acta. 1517(3):460-463.

Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433-506 see also table of contents.

Nishimura, Tetsuya et al., (2000) Identification of a Novel FGF, FGF-21, Preferentially Expressed in the Liver. Biochim Biophys Acta 1492(1):203-206.

Okada-Ban, Mai et al., (2000) Fibroblast growth factor-2. International Journal of Biochemistry & Cell Biology 32(3):263-267.

Olsen, Shaun K. (2003) Fibroblast growth factor (FGF) homologous factors share structural but not functional homology with FGFs. J Biol Chem. 278(36):34226-342236.

Ornitz, David M. et al., (1996) Receptor specificity of the fibroblast growth factor family. J Biol Chem. 271(25)15292-7.

Ornitz, David M. (2000) FGFs, heparan sulfate and FGFRs: Complex interactions essential for development. Bio Essays 22:108-112.

Pellegrini, Luca et al., (2000) Crystal structure of fibroblast growth factor receptor ectodomain bound to ligand and heparin. Nature 407(6807):1029-1034.

Pillai, Omathanu and Panchagnula, Ramesh (2001) Polymers in drug delivery. Curr Opin Chem Biol 5(4):447-451.

Plotnikov, Alexander N. et al., (1999) Structural basis for FGF receptor dimerization and activation. Cell 98(5):641-650.

Plotnikov, Alexander N. et al., (2000) Crystal structures of two FGF-FGFR complexes reveal the determinants of ligand-receptor specificity. Cell 101(4): 413-424.

Sahni, Malika et al., (1999) FGF signaling inhibits chondrocyte proliferation and regulates bone development through the STAT-1 pathway Genes Deve1.13(11):1361-1366.

Schlessinger, Joseph et al., (2000) Crystal structure of a ternary FGF-FGFR-1 Heparin complex reveals a dual role for heparin in FGFR binding and dimerization. Mol Cell 6(3):743-750.

Schmal, H. et al., (2007) bFGF influences human articular chondrocyte differentiation. Cytotherapy 9(2):184-93.

Seno, Masaharu et al., (1990) Carboxyl-terminal structure of basic fibroblast growth factor significantly contributes to its affinity for Heparin. Eur J Biochem. 188:239-245.

Shao, Zhang-Qiang et al., (2006) Effects of intramyocardial administration of slow-release basic fibroblast growth factor on angiogenesis and ventricular remodeling in a rat infarct model. Circ. J. 70(4):471-477.

Skolnik, Jeffrey and Fetrow, Jacquelyn S. (2000) From genes to protein structure and function: novel applications of computational approaches in the genomic era. Trends BioTechnol. 18(1):34-39.

Sleeman, Matthew et al., (2001) Identification of a new fibroblast growth factor receptor, FGFR5. Gene 271(2):171-182.

Smith, Temple and Zhang, Xiaolin (1997) The challenges of genome sequence annotation or The devil is in the details. Nat Biotechnol. 15(12):1222-1223.

Springer, Barry A. et al., (1994) Identification and Concerted Function of Two Receptors Binding Surfaces on Basic Fibroblast Growth Factor Required for Mitogenesis. The Journal of Biological Chemistry 269(43):26879-26884.

Stauber, Deborah J. et al., (2000) Structural interactions of fibroblast growth factor receptor with its ligands. Proc Natl Acad Sci USA 97(1):49-54.

Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23-39.

Wells, James A. (1990) Additivity of mutational effects in proteins. Biochemistry 29(37):8509-8517.

Yamashita, Tetsuo et al., (2000) Identification of a novel fibroblast growth factor, FGF-23, preferentially expressed in the ventrolateral thalamic nucleus of the brain. Biochemical and Biophysical Research Communications 277(2):494-498.

Yayon, Avner et al., (1991) Cell surface, heparin-like molecules are required for binding of basic fibroblast growth factor to its high affinity receptor. Cell 64(4):841-848.

Non-final Office Action for U.S. Appl. No. 12/043,001, mailed May 11, 2011.

Supplemental Search Report for European Patent Application No. 05728956.3, dated May 2, 2011.

Non-final Office Action for U.S. Appl. No. 12/322,996, mailed Apr. 4, 2011.

U.S. Appl. No. 13/025,722, filed Feb. 11, 2011.

Reissue U.S. Appl. No. 12/966,674, filed Dec. 13, 2010.

U.S. Appl. No. 12/931,427, filed Feb. 1, 2011.

Non-final Office Action with regard to U.S. Appl. No. 12/381,072, mailed Jan. 20, 2011.

Non-final Office Action with regard to U.S. Appl. No. 12/924,132, mailed Mar. 1, 2011.

Guilak, Farshid: "Functional Tissue Engineering: The Role of Biomechanics in Articular Cartilage Repair", Clinical Orthopaedics and Related Research, No. 391 S, pp. S295-S305, (c) 2001 Lipponcott Williams & Wilkins, Inc., (11 pages).

Spangenberg, Kimberly, M., et al. "Histomorphometric Analysis of a Cell-Based Model of Cartilage Repair", Tissue Engineering, vol. 6, No. 5, 2002, (8 pages).

Crescenzi et al., "Hyaluronan Linear and Crosslinked Derivatives as Potential/Actual Biomaterials", in Hyaluronan (2002), vol. 1 (Chemical, Biochemical and Biological Aspects), J. F. Kennedy et al., Ed., pp. 251-268.

Michielen et al., "Novel Biomaterials Based on Cross-linked Hyaluronan: Structural Investigations", in Hyaluronan (2002), vol. 1 (Chemical, Biochemical and Biological Aspects), J. F. Kennedy et al., Ed., pp. 269-276.

U.S. Appl. No. 12/657,207, filed Jan. 14, 2010, entitled "Cartilage Particle Tissue Mixtures Optionally Combined With a Cancellous Construct".

International Patent Application No. PCT/US2009/000108, filed Jan. 14, 2010, entitled "Cartilage Particle Tissue Mixtures Optionally Combined With a Cancellous Construct".

Final Office Action mailed Mar. 15, 2010 in connection with U.S. Appl. No. 10/815,778.

Final Office Action mailed Mar. 22, 2010 in connection with U.S. Appl. No. 12/010,984.

U.S. Appl. No. 12/696,366, filed Jan. 29, 2010, entitled "Engineered Osteochondral Construct for Treatment of Articular Cartilage Defects".

First Action Interview Pilot Program Pre-Interview Communication for U.S. Appl. No. 12/328,306, mailed Dec. 22, 2011.

Final Office Action for U.S. Appl. No. 12/328,306, mailed Apr. 19, 2012.

Final Office Action for U.S. Appl. No. 12/881,988, mailed May 11, 2012.

Final Office Action for U.S. Appl. No. 11/081,103, mailed May 18, 2012.

Final Office Action for U.S. Appl. No. 12/179,034, mailed Jan. 27, 2012.

Non-final Office Action for U.S. Appl. No. 12/381,072, mailed Jan. 23, 2012.

Non-final Office Action for U.S. Appl. No. 12/924,132, mailed Feb. 21, 2012.

* cited by examiner

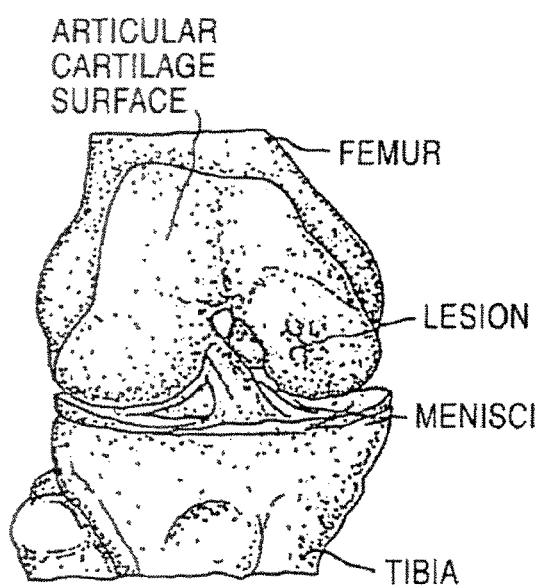
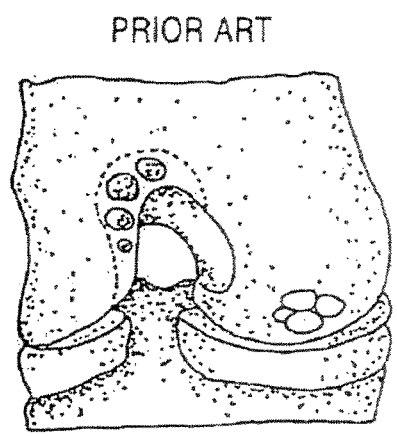
FIG.1
FIG.2

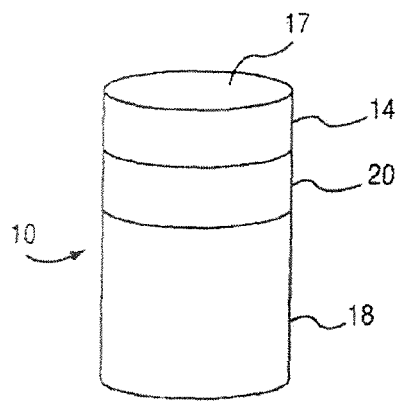
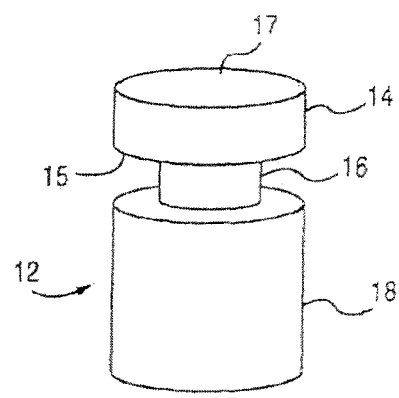
FIG.3  FIG.4
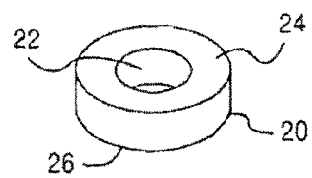
FIG.5
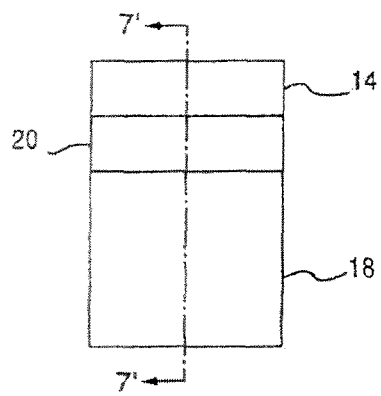
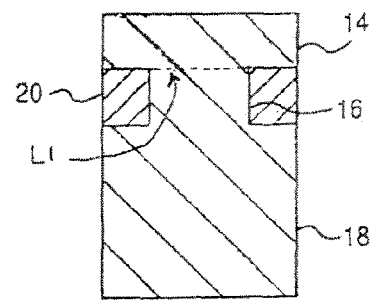
FIG.6  FIG.7

Quantification Of Endogenous TGF-β1 Present In Processed Cartilage Particles

| Donor Number | Age | Sex | Height | Weight (lb.) |
|---|---|---|---|---|
| 53395 | 39 | M | 6'4" | 295 |
| 49212 | 44 | M | 6'0" | 244 |
| 50320 | 20 | M | 6'2" | 231 |
| 45016 | 23 | M | 5'10" | 180 |
| 50768 | 26 | M | 5'6" | 163 |
| 53298 | 25 | M | 5'10" | 174 |
| 53668 | 37 | M | 6'0" | 273 |
| 67278 | 43 | F | 6'0" | 312 |

CANCELLOUS CONSTRUCT WITH SUPPORT RING FOR REPAIR OF OSTEOCHONDRAL DEFECTS

RELATED APPLICATIONS

This application is (i) a continuation-in-part of U.S. Nonprovisional patent application Ser. No. 12/043,001 filed Mar. 5, 2008 now abandoned, which claims priority to U.S. Provisional patent application Ser. No. 60/904,809 filed Mar. 6, 2007; and (ii) a continuation-in-part of U.S. Nonprovisional patent application Ser. No. 12/381,072 filed Mar. 5, 2009, which claims priority to both U.S. Provisional patent application Ser. No. 61/189,252 filed Aug. 15, 2008 and U.S. Provisional patent application Ser. No. 61/205,433 filed Jan. 15, 2009. The disclosure of each and every application referenced above is incorporated herein by reference in its entirety for all purposes.

BACKGROUND OF THE INVENTION

1. Field of Invention

The present invention is generally directed toward an allograft implant construct for osteochondral defect repair and is more specifically directed toward a two piece allograft cancellous bone implant having a cancellous bone base member with a mineralized base section, stem and demineralized top section and a ring-shaped support member which is pulled over the compressed demineralized cancellous top section around the stem. The construct is shaped for an interference fit implantation in a shoulder, knee, hip, or ankle joint, and the construct optionally further contains one or more growth factors impregnated within the construct.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplasties and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans, and water. Active chondrocytes are unique in that they have a relatively low turnover rate and are sparsely distributed within the surrounding matrix. The collagens give the tissue its form and tensile strength and the interaction of proteoglycans with water gives the tissue its stiffness to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited because of its limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age obtain good clinical results, which most likely reflect the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. CARTICEL7 is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with a cambium layer is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and those biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure resulting from the cell cultivation which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The filler osteochondral plugs are harvested from a lower weight-bearing area of lesser importance in the same joint. This technique, shown in Prior Art FIG. 2, can be performed as arthroscopic or open procedures. Reports of results of osteochondral plug autografts in a small number of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct, large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of United States Patents have been specifically directed towards bone plugs which are implanted into a bone defect. Examples of such bone plugs are U.S. Pat. No. 4,950, 296 issued Aug. 21, 1990 which discloses a bone graft device comprising a cortical shell having a selected outer shape and a cavity formed therein for receiving a cancellous plug, which is fitted into the cavity in a manner to expose at least one surface; U.S. Pat. No. 6,039,762 issued Mar. 21, 2000 discloses a cylindrical shell with an interior body of deactivated bone material and U.S. Pat. No. 6,398,811 issued Jun. 4, 2002 directed toward a bone spacer which has a cylindrical cortical bone plug with an internal through going bore designed to hold a reinforcing member. U.S. Pat. No. 6,383,211 issued May 7, 2002 discloses an invertebral implant having a substantially cylindrical body with a through going bore dimensioned to receive bone growth materials.

U.S. Pat. No. 6,379,385 issued Apr. 30, 2002 discloses an implant base body of spongious bone material into which a load carrying support element is embedded. The support element can take the shape of a diagonal cross or a plurality of cylindrical pins. See also, U.S. Pat. No. 6,294,187 issued Sep. 25, 2001 which is directed to a load bearing osteoimplant made of compressed bone particles in the form of a cylinder. The cylinder is provided with a plurality of through going bores to promote blood flow through the osteoimplant or to hold a demineralized bone and glycerol paste mixture. U.S. Pat. No. 6,096,081 issued Aug. 1, 2000 shows a bone dowel with a cortical end cap or caps at both ends, a brittle cancellous body and a through going bore.

The use of implants for cartilage defects is much more limited. Aside from the fresh allograft implants and autologous implants, U.S. Pat. No. 6,110,209 issued Nov. 5, 1998 shows the use of an autologous articular cartilage cancellous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage growth factor, a plurality of cells, or a biological glue. All patients are kept non-weight bearing for four weeks and use a continuous passive motion machine for six hours each night. Histologic appearance of the biopsies has mainly shown a mixture of fibrocartilage with hyaline cartilage. Concerns associated with this method are harvest site morbidity and availability, similar to the mosaicplasty method.

U.S. Pat. No. 6,379,367 issued Apr. 30, 2002 discloses a plug with a base membrane, a control plug, and a top membrane which overlies the surface of the cartilage covering the defective area of the joint.

SUMMARY OF THE INVENTION

In one embodiment, an osteochondral repair allograft construct implant is formed as an unbalanced barbell-shaped cylindrical cancellous bone base member having a mineralized cylindrical base section and a smaller diameter cylindrical stem extending there from leading to a second cylindrical section which is demineralized. In another embodiment, a ring shaped support member is forced over the compressed demineralized second cylindrical section and the aperture of the ring member fits around the stem with a top surface being adjacent the bottom surface of the demineralized cylindrical section and bottom surface being adjacent the upper surface of the mineralized cylindrical base section.

In another embodiment, the allograft construct implant is used to repair osteochondral defects and is placed in a bore which has been cut into the patient to remove the lesion defect area. In another embodiment, each osteochondral repair allograft construct implant can support the addition of a variety of growth factors. In another embodiment, the allograft construct implant can support the addition of a variety of chondrogenic (in any portion of the construct) and/or osteogenic (in any portion of the construct save the demineralized top section) growth factors including, but not limited to morselized allogeneic cartilage, growth factors and variants thereof (FGF-2, FGF-5, FGF-7, FGF-9, FGF-11, FGF-21, IGF-1, TGF-β, TGF-β1, BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist,. hepatocyte growth factor, platelet-derived growth factor, Indian hedgehog and parathyroid hormone-related peptide or bioactive glue. These chondrogrenic and/or osteogenic growth factors or additives can be added throughout the implant or to specific regions of the implant such as the demineralized top section or the mineralized base portion, depending on whether chondrogenesis (any portion of the implant) or osteogenesis (any portion of the implant save the demineralized top section) is the desired outcome.

In another embodiment, the invention provides an allograft implant for joints which provides pain relief, restores normal function and will postpone or alleviate the need for prosthetic replacement.

In another embodiment, the invention provides an osteochondral repair implant which is easily placed in a defect area by the surgeon using an arthroscopic, minimally invasive technique.

In another embodiment, the invention provides an osteochondral repair implant which has load bearing capabilities.

In another embodiment, the invention provides an osteochondral repair procedure which is applicable for both partial and full thickness cartilage lesions that may or may not be associated with damage to the underlying bone.

In another embodiment, the invention provides an implant capable of facilitating bone healing and/or repair of hyaline cartilage.

In another embodiment, the invention provides a cancellous construct which is simultaneously treated with chondrogenic (in any portion of the implant) and/or osteogenic (in any portion of the implant save the demineralized top section) growth factors.

In another embodiment, the invention provides a cancellous construct which is treated with chondrogenic growth factors in the portion of the construct aimed to repair articular cartilage.

In another embodiment, the invention provides a cancellous construct which is treated with chondrogenic growth factors at any portion of the construct.

In another embodiment, the invention provides a cancellous construct which is treated with osteogenic growth factors in any portion of the construct except for the demineralized top portion of the construct.

These and other objects, advantages, and novel features of the present invention will become apparent when considered with the teachings contained in the detailed disclosure along with the accompanying drawings.

BRIEF DESCRIPTION OF THE DRAWINGS

FIG. 1 shows the anatomy of a knee joint;

FIG. 2 shows a schematic mosaicplasty as known in the prior art;

FIG. 3 shows an assembled perspective view of the inventive cartilage repair construct;

FIG. 4 shows a perspective view of the base member of the construct with an unbalanced barbell configuration;

FIG. 5 shows a perspective view of the ring shaped support member of the construct;

FIG. 6 is a side elevation view of the assembled construct; and

FIG. 7 shows a cross section view of the construct of FIG. 6 taken along line 7'-7'.

DESCRIPTION OF THE INVENTION

Figure 8:
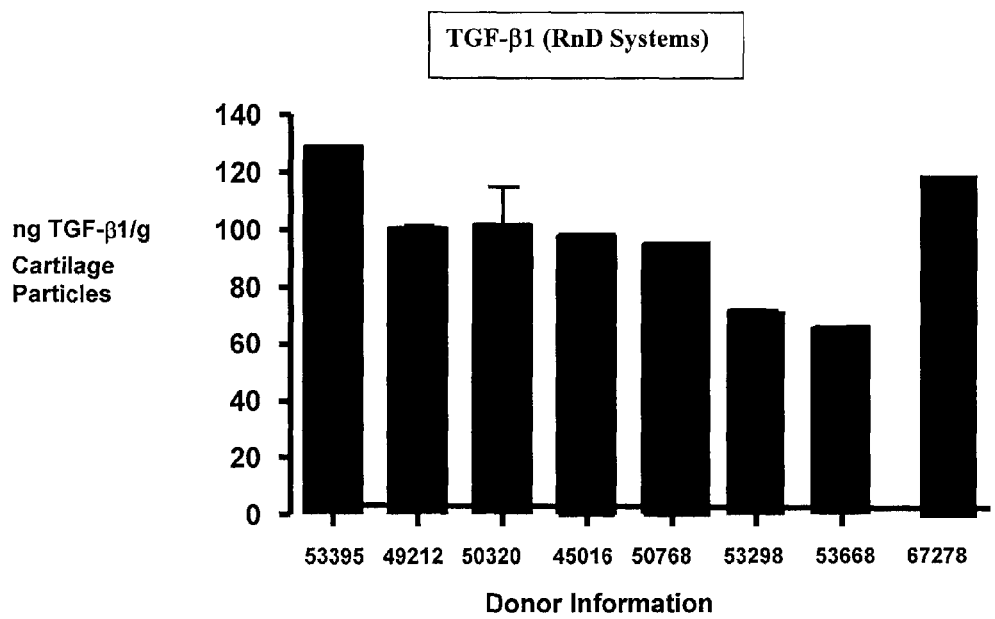
FIG. 8 is a graph showing the relative concentration of endogenous TGF-β1 found in cartilage particles of the present invention, as derived from various donors and manufactured in accordance with Example 1.

The term "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangeably to refer to tissue, material or cells (xenogeneic or allogeneic) which may be introduced into the body of a patient.

The terms "autologous" and "autograft" refer to tissue or cells which originate with or are derived from the recipient, whereas the terms "allogeneic" and "allograft" refer to cells or tissue which originate with or are derived from a donor of the same species as the recipient.

The terms "xenogeneic" and "xenograft" refer to cells or tissue which originate with or are derived from a species other than that of the recipient.

The term "growth factor" means a naturally occurring or synthetic compound capable of stimulating cellular proliferation and/or cellular differentiation. Growth factors are important for regulating a variety of cellular processes.

The term "ELISA" or "Enzyme-Linked ImmunoSorbent Assay" means a biochemical technique used mainly in immunology to detect the presence of an antibody or an antigen in a sample. The ELISA has been used as a diagnostic tool in medicine and plant pathology, as well as a quality control check in various industries. In simple terms, in ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal. Thus in the case of fluorescence ELISA, when light is shone upon the sample, any antigen/antibody complexes will fluoresce so that the amount of antigen in the sample can be measured.

Construct

The present invention is directed towards an osteochondral repair construct constructed of cancellous bone taken from allogenic or xenogenic bone sources.

The construct is preferably derived from dense allograft cancellous bone that may originate from proximal or distal femur, proximal or distal tibia, proximal humerus, talus, calcaneus, patella, or ilium. Cancellous tissue is first processed into blocks and then milled into the desired shapes such as a cylinder for this present invention. A preferred embodiment of the assembled construct 10 is illustrated in FIG. 3. A cancellous bone cylinder is milled using a lathe to form an unbalanced barbell-shaped, primary base member 12, as illustrated in FIGS. 3 and 4. The primary base member 12 includes a top section 14, a cylindrical stem section 16 and a cylindrical base section 18. The top section 14 is milled to have a thickness similar to the thickness of human articular cartilage (e.g., 1.5 -3.5 mm) and the and the diameter of the implant may vary between 5-25 mm. The stem section 16 has a diameter approximately half of the diameter of the entire assembled construct 10. The base section 18 has a thickness or length which is preferably larger than the thickness or length of the top section 14 with a ratio preferably ranging from of at least about 1.5 to 1 to about 6:1. During tissue processing, the top section 14 is substantially demineralized by immersing it in dilute acid while the base section 18 remains mineralized.

Reference is now made to FIGS. 3 and 5, which illustrate a ring-shaped secondary member 20 having an aperture 22 with a diameter equal to or slightly greater than the diameter of the stem 16 and an outer diameter which is the same as the diameter of the top section 14 and base section 18. However, if desired, the aperture 22 can be 10% to 40% larger than the diameter of the stem 16. The top surface 24 and bottom surface 26 of the ring-shaped, or ring, member 20 are preferably planar and after assembly the bottom surface 26 is adjacent the top surface 19 of the base section 18 and the top surface 24 is adjacent the bottom surface 15 of the top section 14. While the ring member 20 is preferably constructed of mineralized allograft cancellous bone, it can be constructed of allograft cortical bone or xenograft bone as long as the same have been decellularized. Alternately, the ring member 20 may be constructed of ceramics or biocompatible polymers.

Demineralization

The top section 14 is substantially demineralized in dilute acid up to a predetermined level (as indicated by broken-line representation L1 in FIG. 7) until the bone contains less than 0.5% wt/wt residual calcium. Subsequently, the resultant tissue form is predominantly Type I collagen, which is sponge-like in nature with an elastic quality. Following decalcification, the tissue is further cleaned, brought to a physiological pH level of about 7 and may also be treated so that the cancellous tissue is non-osteoinductive. This inactivation of inherent osteoinductivity may be accomplished via chemical or thermal treatment or by high energy irradiation. The cancellous top section 14 is preferably treated with an oxidizing agent such as hydrogen peroxide in order to render it non-osteoinductive.

Following demineralization the top section 14 is spongy and deformable allowing it to be squeezed through the center aperture 22 of the ring member 20. After the implant has been assembled, morselized cartilage particles combined with a carrier or growth factor may be added to the top section 14. If desired, the open cancellous structure of the top section 14 may be loaded with a cartilage paste or gel as noted below and/or one or more additives namely recombinant or native or variant growth factors (FGF-2, FGF-5, FGF-7, FGF-9, FGF-11, FGF-21, IGF-1, TGF-β1, BMP-2, BMP-4, BMP-7, PDGF, VEGF), human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog, parathyroid hormone-related peptide, viral vectors for growth factor or DNA delivery, nanoparticles, or platelet-rich plasma. This design enables the fabrication of an implant that possesses a relatively uniform substantially demineralized top section that is distinct from the mineralized base section.

Incorporation of Additives into the Construct

The demineralized portion of the construct can be provided with a matrix of cartilage putty or gel consisting of minced or milled allograft cartilage which has been lyophilized so that its water content ranges from about 0.1% to about 8.0% ranging from about 25% to about 50% by weight, mixed with a carrier of sodium hyaluronate solution (HA) (molecular weight ranging from about $7.0 \times 10^5$ to about $1.2 \times 10^6$) or any other bioabsorbable carrier such as hyaluronic acid and its derivatives, gelatin, collagen, chitosan, alginate, buffered PBS, Dextran CMC, or other polymers, the carrier ranging from about 75% to about 25% by weight. In one embodiment, the cartilage is minced or milled to a size less than or equal to about 212 μm. In another embodiment, the cartilage is minced or milled to a size of from about 5 μm to about 212 μm. In another embodiment, the cartilage is minced or milled to a size of from about 6 μm to about 10 μm. In another embodiment, the cartilage can be minced or milled to a size of less than or equal to about 5 μm. The small size of the minced or milled particulate cartilage can facilitate increased exposure or release of various growth factors due to the increased aggregate surface area of the particulate cartilage used.

The cartilage particles can contain endogenous growth factors. These endogenous growth factors can be extracted from the cartilage particles by the method outlined in Example 1 and detected by the method outlined in Example 2. Exogenous growth factors can also be combined with the cartilage particulate. In one embodiment, cartilage is recovered from deceased human donors, and the tissue may be treated with any known method or methods for chemically cleaning or treating a soft tissue. The cartilage is then lyophilized, milled, then sieved to yield particle sizes of, on average, less than or equal to 212 microns. The cartilage particles are mixed with a growth factor in an aqueous vehicle, then the particles can either be lyophilized and stored dry at room temperature or frozen, or used immediately. For example, particles containing chondrogenic growth factor can be added to any portion of the allograft construct, and particles containing osteogenic growth factor can be added to any portion of the allograft construct save the demineralized cancellous cap. The mixture containing the cartilage particles and growth factor can be lyophilized for storage.

The growth factor can be any one of a variety of growth factors known to promote wound healing, cartilage and/or bone development (e.g. BMP's particturlarly BMP-2, FGF's particularly FGF-2 and-9 and/or variants of FGF-2, IGF, VEGF, PDGF, etc.). The vehicle used to solubilize the growth factor and adsorb it into the cartilage particles can be saline, water, PBS, Ringers, etc.

In one embodiment, the resulting enhanced cartilage particles can contain levels of growth factors that are greater than that found in intact cartilage. In another embodiment, the cartilage particle mixture can be infused into all or part of the construct. If desired, the cartilage particle mixture can be infused primarily into the demineralized end of the primary member of the construct.

It is further envisioned that cells which have been collected from the patient or grown outside the patient can be inserted into the entire construct or into the cancellous demineralized top section 14 matrix before, during or after deposit of the construct 10 into the defect area. Such cells include, for example, allogenic or autologous bone marrow cells, stem cells and chondrocyte cells. The cellular density of the cells preferably ranges from $1.0 \times 10^8$ to $5.0 \times 10^8$ or from about 100 million to about 500 million cells per cc of putty or gel mixture.

Placement of Construct

The construct 10 is placed in an osteochondral defect area bore which has been cut in the lesion area of a patient with the upper surface 17 of the top section 14 being slightly proud (i.e., above), slightly below, or substantially flush with the surface of the original cartilage surrounding the defect area remaining at the site being treated. The construct 10 has a length which can be the same as the depth of the defect or more or less than the depth of the bore. If the construct 10 is the same as the depth of the bore, the base of the implant is supported by the bottom surface of the bore and the top surface 17 is substantially level with the articular cartilage. If the construct 10 is of a lesser length, the base of the construct is not supported but support is provided by the wall of the defect area bore or respective cut out area as the plug is interference fit within the bore or cut out area with the cap being slightly proud, slightly below, or flush with the surrounding articular cartilage depending on the surgeon's preference. With such load bearing support, the graft surface is not damaged by weight or bearing loads which can cause micromotion interfering with the graft interface producing fibrous tissue interfaces and subchondral cysts.

In operation, the lesion or defect is removed by cutting a blind bore removing a lesion in the implant area. The construct 10 is then placed in the bore or cut away area in an interface fit with the surrounding walls.

If the construct is moveable within the bore, suitable organic glue material can be used to keep the implant fixed in place in the implant area. Suitable organic glue material can also be used to keep the additives in the construct within the construct following implantation into the defect site. Suitable organic glue material can be found commercially, such as for example: TISSEEL 7 or TISSUCOL 7 (fibrin based adhesive; Immuno AG, Austria), Adhesive Protein (Sigma Chemical, USA), Dow Corning Medical Adhesive B (Dow Corning, USA), fibrinogen thrombin, elastin, collagen, casein, albumin, keratin and the like.

EXAMPLES

Example 1

Processed Cartilage Particle Extraction

Cartilage is recovered from deceased human donors, and the tissue may be treated with any known method or methods for chemically cleaning or treating a soft tissue. The cartilage is then lyophilized, freeze-milled, then sieved to yield particle sizes of, on average, less than or equal to 212 microns,. The cartilage particles are -again lyophilized prior to storage or extraction. The particles are extracted in guanidine HCl by incubating at 4° C. on an orbital shaker at 60 rpm for 24 hr, followed by dialysis (8 k MWCO membrane dialysis tube) in 0.05M Tris HCl for 15 hrs at 4° C. The dialysis solution was then replaced and the dialysis continued for another 8 hrs at 4° C. The post-dialysis extracts were stored at −70° C. until ELISA analysis.

Example 2

Quantification Of Endogenous Growth Factors Present In Processed Cartilage 0.25 g of cartilage particles were weighed out for each donor. The cartilage particles were transferred to tubes containing 5 ml of extraction solution (4M Guanidine HCl in TrisHCl). The cartilage particles were incubated at 4° C. on the orbital shaker at 60 rpm for 24 hr, followed by dialysis (8 k MWCO membrane dialysis tube) in 0.05M TrisHCl for 15 hrs at 4° C. The dialysis solution was then replaced and the dialysis continued for another 8 hrs at 4° C. The post-dialysis extracts were stored at −70° C. until ELISA run. Notably, the above protocol can also be utilized in order to determine the total growth factor concentration (e.g., exogenous plus endogenous) present in a device of the instant invention.

FIG. 8 illustrates the relative concentration of endogenous TGF-$\beta 1$ found in cartilage particles of the present invention as derived from various donors and manufactured in accordance with Example 1.

Figure 9:
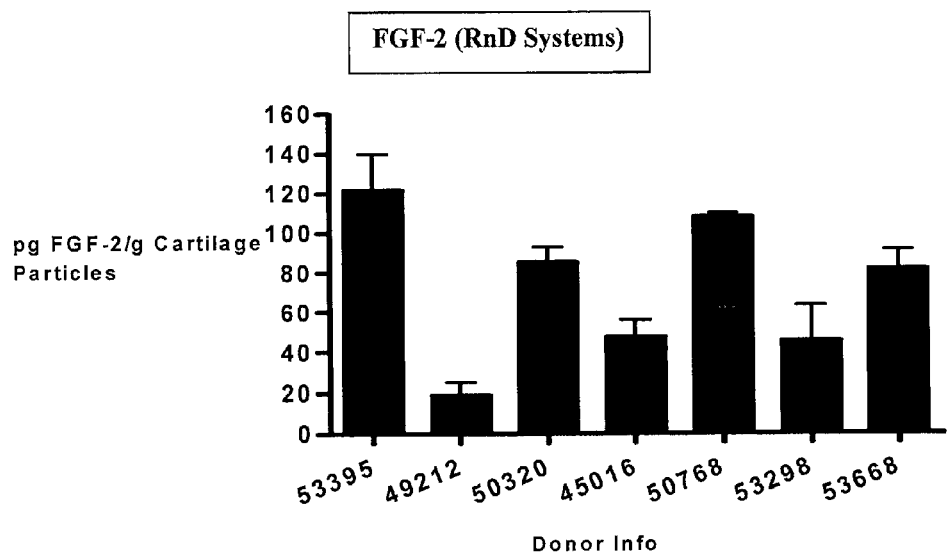
FIG. 9 is a graph showing the relative concentration of endogenous FGF-2 found in cartilage particles of the present invention, as derived from various donors and manufactured in accordance with Example 1.

FIG. 9 illustrates the relative concentration of endogenous FGF-2 found in cartilage particles of the present invention as derived from various donors and manufactured in accordance with Example 1.

Figure 10:
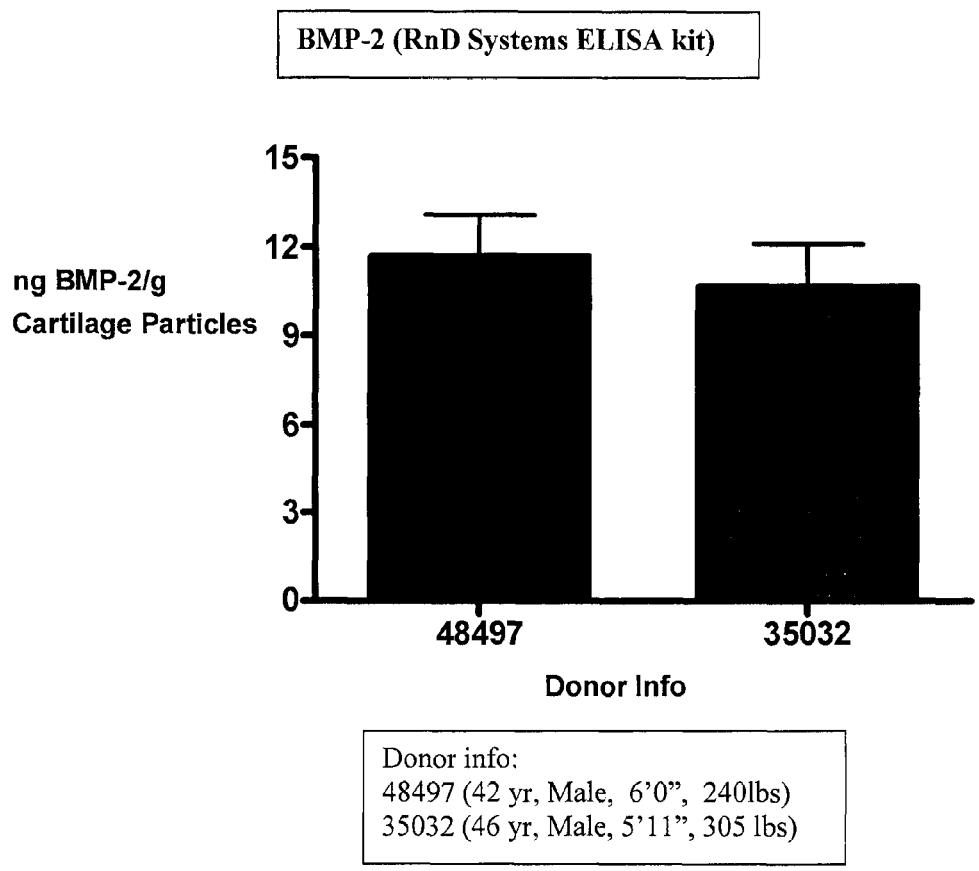
FIG. 10 is a graph showing the relative concentration of endogenous BMP-2 found in cartilage particles of the present invention, as derived from various donors and manufactured in accordance with Example 1.

FIG. 10 illustrates the relative concentration of endogenous BMP-2 found in cartilage particles of the present invention as derived from various donors and manufactured in accordance with Example 1.

The results shown in FIG. 8 indicate that processed cartilage particles prepared in accordance with the method of Example 1 retain a concentration of endogenous TGF-$\beta 1$. The results shown in FIG. 9 indicate that processed cartilage particles prepared in accordance with the method of Example 1 also retain concentrations of endogenous FGF-2. The results shown in FIG. 10 indicate that processed cartilage particles prepared in accordance with the method of Example 1 also retain concentrations of endogenous BMP-2.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims.

What we claim is:

1. A construct for repairing an osteochondral defect, comprising:
    a ring-shaped member having a top surface, a bottom surface, an outer diameter and an inner diameter, said inner diameter being defined by an aperture extending from said top surface to said bottom surface; and
    a base member derived from bone and having a longitudinal axis, which defines an axial direction, said base member having
        a first section arranged along said longitudinal axis proximate a first end of said base member, said first section being substantially mineralized and having a first diameter,
        a stem section arranged along said longitudinal axis, said stem section having one end attached to said first section and a second diameter that is less than said first diameter, and
        a second section arranged along said longitudinal axis proximate a second end of said base member opposite said first end thereof, said second section having a top surface, a bottom surface, and a thickness that substantially matches the thickness of a patient's surrounding native articular cartilage layer, said second section being attached to another end of said stem section opposite said one end thereof, and said second section being substantially demineralized to thereby provide said second section with an elastic quality that renders said second section deformable from a first condition, in which said second section has a third diameter that is greater than said inner diameter of said ring-shaped member, to a second condition, in which said second section is insertable through said aperture of said ring-shaped member, whereby said ring-shaped member is mountable around said stem section between said first and second sections such that said bottom surface of said second section engages said top surface of said ring-shaped member.

2. The construct as recited in claim 1, wherein each of said first and second sections has a cylindrical shape; and wherein said stem section has a cylindrical shape and said second diameter thereof is smaller than said first diameter of said first section and smaller than said third diameter of said second section, whereby said base member has a barbell-like shape.

3. The construct as recited in claim 1, wherein said ring-shaped member is formed from allograft bone.

4. The construct as recited in claim 1, wherein said second section of said base member is non-osteoinductive.

5. The construct as recited in claim 1, wherein said base member is formed from allograft cancellous bone.

6. The construct as recited in claim 1, wherein said inner diameter of said ring-shaped member is similar to said second diameter of said stem section.

7. The construct as recited in claim 1, wherein said inner diameter of said ring-shaped member is larger than said second diameter of said stem section by about 10% to about 40%.

8. The construct as recited in claim 1, wherein said ring-shaped member is constructed of materials taken from a group consisting of allograft bone, xenograft bone, ceramics and biocompatible plastic polymers.

9. The construct as recited in claim 1, wherein said second section of said base member contains milled allograft cartilage particles.

10. The construct as recited in claim 9, wherein said second section of said base member also contains a biocompatible carrier for said cartilage particles.

11. The construct as recited in claim 9, wherein said cartilage particles contain growth factors.

12. The construct as recited in claim 11, wherein said growth factors are selected from the group consisting of TGF-β, FGF-2 and BMP-2.

13. The construct as recited in claim 9, wherein said cartilage particles contain at least one additive taken from a group consisting of growth factors, variants of said growth factors, human chondrocytes, human bone marrow cells, stem cells, insulin, insulin-like growth factor-1, transforming growth factor-B, interleukin-1 receptor antagonist, hepatocyte growth factor, platelet-derived growth factor, Indian hedgehog and parathyroid hormone-related peptide, bioactive glue, viral vectors for growth factor or DNA delivery, nanoparticles, and platelet-rich plasma.

14. The construct as recited in claim 13, wherein said growth factors include FGF-2, FGF-5, FGF-7, FGF-9, FGF-11 and FGF-21.

15. The construct as recited in claim 9, wherein said cartilage particles are freeze-milled.

16. The construct as recited in claim 1, wherein at least one of said base member and said ring-shaped member contains at least one additive taken from a group consisting of growth factors, variants of said growth factors, human chondrocytes, human bone marrow cells, stem cells, demineralized bone matrix, cartilage particles, insulin, insulin-like growth factor-1, transforming growth factor-B, interleukin-1 receptor antagonist, hepatocyte growth factor, platelet-derived growth factor, Indian hedgehog and parathyroid hormone-related peptide, bioactive glue, viral vectors for growth factor delivery, viral vectors for DNA delivery, nanoparticles, and platelet-rich plasma.

17. The construct as recited in claim 16, wherein said second section of said base member contains said at least one additive.

18. The construct as recited in claim 1, wherein said second section of said base member contains at least one chondrogenic additive and said first section of said base member contains at least one osteogenic additive.

19. The construct as recited in claim 9, wherein said cartilage particles have a size within a range of from about 10 microns to about 212 microns.

20. The construct as recited in claim 1, whereby said first and second sections of said base member are arranged coaxially relative to said longitudinal axis of said base member.

21. The construct as recited in claim 20, wherein said stem section of said base member is arranged coaxially relative to said first and second sections of said base member.

* * * * *